United States Patent
Inoue et al.

(10) Patent No.: US 11,036,136 B2
(45) Date of Patent: Jun. 15, 2021

(54) ONIUM SALT, CHEMICALLY AMPLIFIED POSITIVE RESIST COMPOSITION, AND RESIST PATTERN FORMING PROCESS

(71) Applicant: Shin-Etsu Chemical Co., Ltd., Tokyo (JP)

(72) Inventors: Naoya Inoue, Joetsu (JP); Satoshi Watanabe, Joetsu (JP); Daisuke Domon, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 144 days.

(21) Appl. No.: 16/420,680

(22) Filed: May 23, 2019

(65) Prior Publication Data

US 2019/0361350 A1   Nov. 28, 2019

(30) Foreign Application Priority Data

May 25, 2018 (JP) .............. JP2018-100517

(51) Int. Cl.
| | | |
|---|---|---|
| *C07C 309/73* | (2006.01) | |
| *G03F 7/039* | (2006.01) | |
| *C08F 220/28* | (2006.01) | |
| *C08F 220/38* | (2006.01) | |
| *C08G 61/02* | (2006.01) | |
| *G03F 7/038* | (2006.01) | |
| *G03F 7/20* | (2006.01) | |
| *G03F 7/004* | (2006.01) | |

(52) U.S. Cl.
CPC .......... *G03F 7/0395* (2013.01); *C07C 309/73* (2013.01); *C08F 220/28* (2013.01); *C08F 220/38* (2013.01); *C08G 61/02* (2013.01); *G03F 7/0045* (2013.01); *G03F 7/0382* (2013.01); *G03F 7/0397* (2013.01); *G03F 7/2004* (2013.01); C08F 220/281 (2020.02); C08F 220/283 (2020.02); C08F 220/382 (2020.02); C08G 2261/1452 (2013.01)

(58) Field of Classification Search
CPC . G03F 7/0395; G03F 1/78; G03F 1/76; G03F 7/2037; G03F 7/038; G03F 7/2059; G03F 7/0046; G03F 7/027; G03F 7/0388; G03F 7/004; G03F 7/039; G03F 7/0382; G03F 7/0397; G03F 7/2004; G03F 7/20; G03F 7/0045; G03F 7/322; G03F 7/0392; C08F 220/28; C08F 220/38; C08F 220/281; C08F 220/283; C08F 220/382; C08G 61/02; C08G 2261/1452; C07D 339/08; C07D 493/08; C07D 327/08; C07D 333/76; C07D 335/12; C07D 279/20; C07D 335/16; C07C 381/12; C07C 309/42; C07C 305/24; C07C 2601/14; C07C 2603/74; C07C 2601/20; C07C 2601/08; C07C 309/73; C08K 5/42; C09K 3/00

See application file for complete search history.

(56) References Cited

U.S. PATENT DOCUMENTS

| | | | |
|---|---|---|---|
| 7,527,912 B2 | 5/2009 | Ohsawa et al. | |
| 8,361,693 B2 | 1/2013 | Masunaga et al. | |
| 8,900,791 B2 | 12/2014 | Tsuchimura et al. | |
| 9,604,921 B2 | 3/2017 | Domon et al. | |
| 2014/0349223 A1* | 11/2014 | Kawabata | G03F 7/0388 430/18 |
| 2016/0090355 A1* | 3/2016 | Domon | G03F 7/0045 430/5 |

FOREIGN PATENT DOCUMENTS

| | | | |
|---|---|---|---|
| JP | 2009-53518 A | | 3/2009 |
| JP | 2010-100604 A | | 5/2010 |
| JP | 2011-22564 A | | 2/2011 |
| JP | 5083528 B2 | | 11/2012 |
| JP | 2015090457 A | * | 5/2015 |
| JP | 6248882 B2 | | 12/2017 |

OTHER PUBLICATIONS

English Translation of JP 2015-090457 A; Hayato Namai; Published: May 11, 2015 (Year: 2015).*

* cited by examiner

*Primary Examiner* — John A McPherson
*Assistant Examiner* — Richard David Champion
(74) *Attorney, Agent, or Firm* — Westerman, Hattori, Daniels & Adrian, LLP

(57) ABSTRACT

An onium salt of arenesulfonic acid having a bridged ring-containing group generates a bulky acid having an appropriate strength and controlled diffusion. When a positive resist composition comprising the onium salt and a base polymer is processed by lithography, a pattern of rectangular profile having high resolution and reduced LER is formed.

12 Claims, No Drawings

ONIUM SALT, CHEMICALLY AMPLIFIED POSITIVE RESIST COMPOSITION, AND RESIST PATTERN FORMING PROCESS

CROSS-REFERENCE TO RELATED APPLICATION

This non-provisional application claims priority under 35 U.S.C. § 119(a) on Patent Application No. 2018-100517 filed in Japan on May 25, 2018, the entire contents of which are hereby incorporated by reference.

TECHNICAL FIELD

This invention relates to an onium salt, chemically amplified positive resist composition, and resist pattern forming process.

BACKGROUND ART

To meet the recent demand for higher integration in integrated circuits, pattern formation to a finer feature size is required. Acid-catalyzed chemically amplified resist compositions are most often used in forming resist patterns with a feature size of 0.2 μm or less. High-energy radiation such as UV, deep-UV or electron beam (EB) is used as the energy source for exposure of these resist compositions. In particular, while EB lithography is utilized as the ultra-fine microfabrication technique, it is also indispensable in processing a photomask blank to form a photomask for use in semiconductor device fabrication.

The resist compositions for use in photolithography include positive tone compositions wherein a pattern is formed after the exposed region is dissolved and negative tone compositions wherein the exposed region is left to form a pattern. A choice may be made depending on the desired resist pattern structure.

In general, the EB lithography is by writing an image with EB, without using a mask. In the case of positive resist, those regions of a resist film other than the regions to be retained are successively irradiated with EB having a minute area. In the case of negative resist, those regions of a resist film to be retained are successively irradiated with EB.

The operation of successively scanning all finely divided regions on the work surface takes a long time as compared with full wafer exposure through a photomask. In order to avoid any decline of throughput, the resist film must be highly sensitive. Because of the long image-writing time, there is a likelihood of a difference arising between the initially written portion and the later written portion. Thus the stability with time of exposed regions in vacuum is one of important performance requirements. One of the important applications of chemically amplified resist material resides in processing of photomask blanks. Some photomask blanks have a surface material that can have an impact on the pattern profile of the overlying chemically amplified resist film, such as a layer of a chromium compound, typically chromium oxide deposited on a photomask substrate. For high resolution and profile retention after etching, it is one important performance factor to maintain the pattern profile of resist film rectangular independent of the type of substrate.

The control of resist sensitivity and pattern profile as mentioned above has been improved by a proper selection and combination of resist material-constituting components and processing conditions. One outstanding improvement is directed to the diffusion of acid that largely affects the resolution of a chemically amplified resist film. In the processing of photomasks, it is required that the profile of a resist pattern formed as above do not change with a lapse of time from the end of exposure to PEB. The major cause of such a change with time is diffusion of an acid generated upon exposure. The problem of acid diffusion has been widely studied not only in the field of photomask processing, but also in the field of general resist films because it has a significant impact on sensitivity and resolution.

Patent Documents 1 and 2 describe acid generators capable of generating bulky acids for controlling acid diffusion and reducing roughness. Since these acid generators are still insufficient to control acid diffusion, it is desired to have an acid generator with more controlled diffusion.

Patent Document 3 discloses a resist composition comprising a base resin to which a sulfonic acid to be generated upon light exposure is bound so that the acid diffusion is controlled. This approach of controlling acid diffusion by binding recurring units capable of generating acid upon exposure to a base polymer is effective in forming a pattern with minimal LER. However, a problem arises with respect to the solubility in organic solvent of the base polymer having bound therein recurring units capable of generating acid upon exposure, depending on the structure and proportion of such recurring units.

Polymers comprising a major proportion of aromatic structure having an acidic side chain, for example, polyhydroxystyrene have been widely used in resist materials for the KrF excimer laser lithography. These polymers are not used in resist materials for the ArF excimer laser lithography since they exhibit strong absorption at a wavelength around 200 nm. These polymers, however, are expected to form useful resist materials for the EB and EUV lithography for forming patterns of finer size than the processing limit of ArF lithography because they offer high etching resistance.

Often used as the base polymer in positive resist compositions for EB and EUV lithography is a polymer having an acidic functional group on phenol side chain masked with an acid labile (protective) group wherein the acid labile (protective) group is deprotected by the catalysis of an acid generated from a photoacid generator upon exposure to high-energy radiation so that the polymer may become soluble in alkaline developer. Typical of the acid labile group are tertiary alkyl, tert-butoxycarbonyl, and acetal groups. On use of protective groups requiring a relatively low level of activation energy for deprotection such as acetal groups, a resist film having a high sensitivity is advantageously obtainable. However, if the diffusion of generated acid is not fully controlled, deprotection reaction can occur even in the unexposed regions of the resist film, giving rise to problems like degradation of LER and a lowering of in-plane uniformity of pattern line width (or CDU).

Patent Document 4 describes a resist composition comprising a resin comprising recurring units having an acetal group and a sulfonium salt capable of generating an acid having a high pKa such as fluoroalkanesulfonic acid. Regrettably, the pattern obtained therefrom has substantial LER. This is because the acid strength of fluoroalkanesulfonic acid is too high for the deprotection of an acetal group requiring a relatively low level of activation energy for deprotection. So, even if acid diffusion is controlled, deprotection reaction can occur in the unexposed region with a minor amount of acid diffused thereto.

CITATION LIST

Patent Document 1: JP-A 2009-053518
Patent Document 2: JP-A 2010-100604

Patent Document 3: JP-A 2011-022564
Patent Document 4: JP 5083528
Patent Document 5: JP 6248882

DISCLOSURE OF INVENTION

Recently, there is the demand for resist compositions capable of forming not only line-and-space (LS), isolated line (IL) and isolated space (IS) patterns of satisfactory profile, but also hole patterns of satisfactory profile. Patent Document 5 describes an acid generator capable of generating a bulky acid with controlled diffusion, from which patterns having satisfactory resolution and roughness are obtainable, but the formation of hole patterns is accompanied with corner rounding.

An object of the invention is to provide an onium salt capable of generating an acid having an appropriate strength and controlled diffusion, a chemically amplified positive resist composition, and a resist pattern forming process using the resist composition.

The inventors have found that an onium salt of arenesulfonic acid having a bridged ring-containing group generates a bulky acid which is controlled in diffusion, a pattern with high resolution and minimal LER is obtainable from a resist composition comprising the onium salt, and especially, a hole pattern of rectangular profile is obtainable by virtue of properly inhibited dissolution.

In one aspect, the invention provides an onium salt having the formula (1).

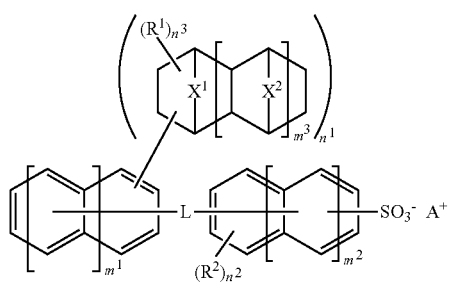

(1)

Herein $X^1$ and $X^2$ are each independently methylene, propane-2,2-diyl or ether bond; L is a single bond, ester bond, sulfonic acid ester bond, carbonate bond or carbamate bond; $R^1$ and $R^2$ are each independently a $C_1$-$C_{20}$ monovalent hydrocarbon group which may contain a heteroatom; $m^1$ and $m^2$ are each independently an integer of 0 to 2, $m^3$ is 0 or 1, $n^1$ is an integer satisfying $1 \leq n^1 \leq 5+2m^1$, $n^2$ is an integer satisfying $0 \leq n^2 \leq 4+2m^2$, $n^3$ is an integer satisfying $0 \leq n^3 \leq 8+4m^3$; $A^+$ is a sulfonium cation having the formula (2), an iodonium cation having the formula (3), or an ammonium cation having the formula (4):

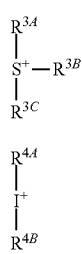

(2)

(3)

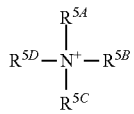

(4)

wherein $R^{3A}$, $R^{3B}$, $R^{3C}$, $R^{4A}$, $R^{4B}$, $R^{5A}$, $R^{5B}$ and $R^{5C}$ are each independently a $C_1$-$C_{20}$ monovalent hydrocarbon group which may contain a heteroatom, $R^{5D}$ is hydrogen or a $C_1$-$C_{20}$ monovalent hydrocarbon group which may contain a heteroatom, any two of $R^{3A}$, $R^{3B}$, and $R^{3C}$, or any two of $R^{5A}$, $R^{5B}$, $R^{5C}$, and $R^{5D}$ may bond together to form a ring with the sulfur or nitrogen atom to which they are attached.

In another aspect, the invention provides a chemically amplified positive resist composition comprising (A) an acid generator containing the onium salt defined above and (B) a base polymer containing a polymer adapted to be decomposed under the action of acid to increase its solubility in alkaline developer.

Typically, the polymer comprises recurring units having the formula (B1).

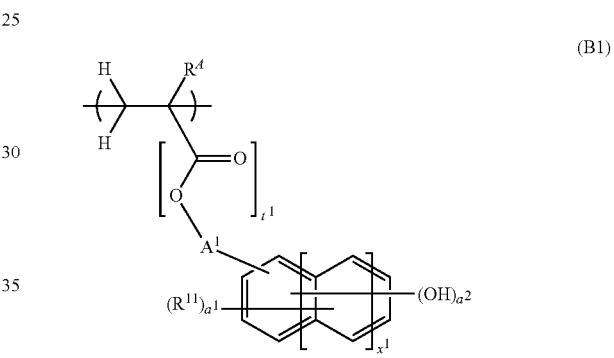

(B1)

Herein $R^A$ is hydrogen, fluorine, methyl or trifluoromethyl; $R^{11}$ is each independently halogen, an optionally halogenated $C_2$-$C_8$ acyloxy group, optionally halogenated $C_1$-$C_6$ alkyl group, or optionally halogenated $C_1$-$C_6$ alkoxy group; $A^1$ is a single bond or $C_1$-$C_{10}$ alkanediyl group in which an ether bond may intervene in a carbon-carbon bond; $t^1$ is 0 or 1, $x^1$ is an integer of 0 to 2, $a^1$ is an integer satisfying $0 \leq a^1 \leq 5+2x^1-a^2$, and $a^2$ is an integer of 1 to 3.

In a preferred embodiment, the polymer comprises recurring units having the formula (B2).

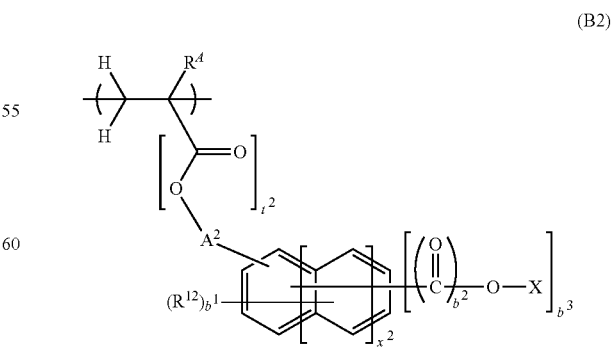

(B2)

Herein $R^A$ is hydrogen, fluorine, methyl or trifluoromethyl; $R^{12}$ is each independently halogen, an optionally halogenated $C_2$-$C_8$ acyloxy group, optionally halogenated $C_1$-$C_6$ alkyl group, or optionally halogenated $C_1$-$C_6$ alkoxy group; $A^2$ is a single bond or $C_1$-$C_{10}$ alkanediyl group in which an ether bond may intervene in a carbon-carbon bond; $t^2$ is 0 or 1, $x^2$ is an integer of 0 to 2, $b^1$ is an integer satisfying $0 \leq b^1 \leq 5+2x^2-b^3$, $b^2$ is 0 or 1, $b^3$ is an integer of 1 to 3, X is an acid labile group in case of $b^3=1$, and X is each independently hydrogen or an acid labile group in case of $b^3=2$ or 3, at least one X being an acid labile group.

In a preferred embodiment, the polymer comprises recurring units of at least one type selected from units having the formulae (B3), (B4), and (B5).

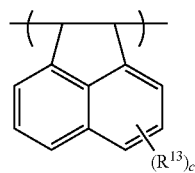
(B3)

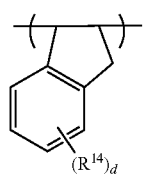
(B4)

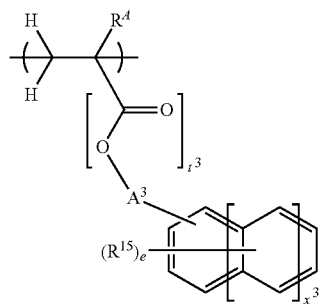
(B5)

Herein $R^A$ is hydrogen, fluorine, methyl or trifluoromethyl; $R^{13}$ and $R^{14}$ are each independently a hydroxyl group, halogen atom, acetoxy group, optionally halogenated $C_1$-$C_6$ alkyl group, optionally halogenated $C_1$-$C_6$ primary alkoxy group, optionally halogenated $C_2$-$C_6$ secondary alkoxy group, optionally halogenated $C_2$-$C_8$ acyloxy group, or optionally halogenated $C_2$-$C_8$ alkylcarbonyloxy group; $R^{15}$ is an acetyl group, acetoxy group, $C_1$-$C_{20}$ alkyl group, $C_1$-$C_{20}$ primary alkoxy group, $C_2$-$C_{20}$ secondary alkoxy group, $C_2$-$C_{20}$ acyloxy group, $C_2$-$C_{20}$ alkoxyalkyl group, $C_2$-$C_{20}$ alkylthioalkyl group, halogen atom, nitro group, or cyano group; $A^3$ is a single bond or $C_1$-$C_{10}$ alkanediyl group in which an ether bond may intervene in a carbon-carbon bond; c is an integer of 0 to 6, d is an integer of 0 to 4, e is an integer of 0 to 5, $t^3$ is 0 or 1, and $x^3$ is an integer of 0 to 2.

In a preferred embodiment, the polymer further comprises recurring units of at least one type selected from units having the formulae (B6) to (B11).

(B6)

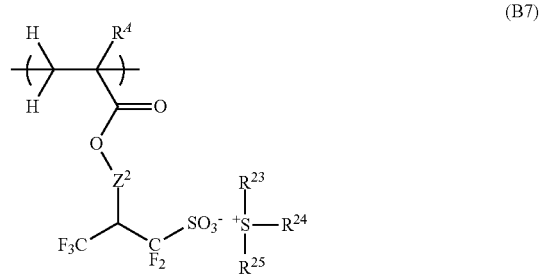
(B7)

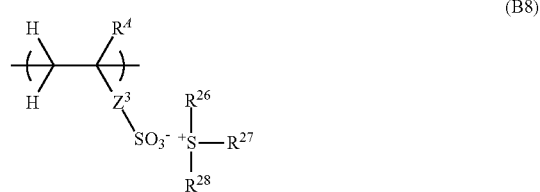
(B8)

(B9)

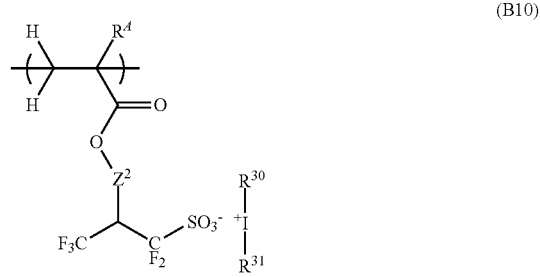
(B10)

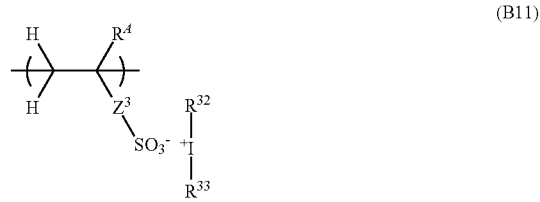
(B11)

Herein $R^A$ is hydrogen, fluorine, methyl or trifluoromethyl; $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl, $C_2$-$C_6$ alkenediyl or phenylene group, which may contain a carbonyl, ester bond, ether bond or hydroxyl moiety; $Z^2$ is a single bond or —$Z^{21}$—C(=O)—O—, $Z^{21}$ is a $C_1$-$C_{20}$ divalent hydrocarbon group which may contain a heteroatom; $Z^3$ is each independently a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ alkanediyl, $C_2$-$C_6$ alkenediyl or phenylene group, which may contain a carbonyl, ester bond, ether bond or hydroxyl moiety; $R^{21}$ to $R^{33}$ are each independently a $C_1$-$C_{20}$ monovalent hydrocarbon group which may contain a heteroatom, or $R^{11}$ and $R^{22}$ may bond together to form a ring with the sulfur atom to which they are attached, or any two of $R^{23}$, $R^{24}$ and $R^{25}$ may bond together to form a ring with the sulfur atom to which they are attached, any two of $R^{26}$, $R^{27}$ and $R^{28}$ may bond together to form a ring with the sulfur atom to which they are attached; and $M^-$ is a non-nucleophilic counter ion.

The resist composition may further comprise (C) an organic solvent.

The resist composition may further comprise (D) a fluorinated polymer comprising recurring units having the formula (D1) and recurring units of at least one type selected from units having the formulae (D2), (D3), (D4), and (D5).

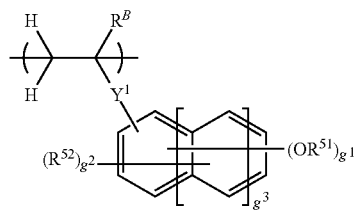
(D1)

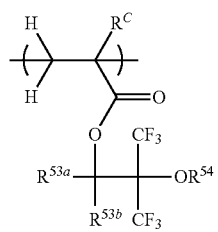
(D2)

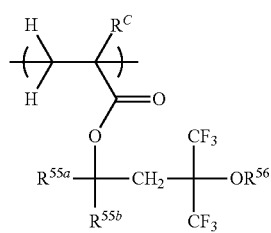
(D3)

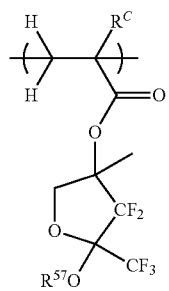
(D4)

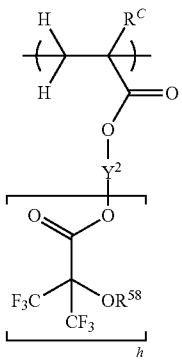
(D5)

Herein $R^B$ is hydrogen or methyl; $R^C$ is each independently hydrogen, fluorine, methyl or trifluoromethyl; $R^{51}$ is hydrogen or a $C_1$-$C_5$ straight or branched monovalent hydrocarbon group in which a heteroatom-containing moiety may intervene in a carbon-carbon bond; $R^{52}$ is a $C_1$-$C_5$ straight or branched monovalent hydrocarbon group in which a heteroatom-containing moiety may intervene in a carbon-carbon bond; $R^{53a}$, $R^{53b}$, $R^{55a}$ and $R^{55b}$ are each independently hydrogen or a $C_1$-$C_{10}$ alkyl group; $R^{54}$, $R^{56}$, $R^{57}$ and $R^{58}$ are each independently hydrogen, a $C_1$-$C_{15}$ monovalent hydrocarbon group, $C_1$-$C_{15}$ monovalent fluorinated hydrocarbon group, or an acid labile group, with the proviso that an ether bond or carbonyl moiety may intervene in a carbon-carbon bond in the monovalent hydrocarbon groups or monovalent fluorinated hydrocarbon groups represented by $R^{54}$, $R^{56}$, $R^{57}$ and $R^{58}$; $Y^1$ is a single bond, —C(=O)—O— or —C(=O)—NH—; $Y^2$ is a $C_1$-$C_{20}$ (h+1)-valent hydrocarbon group or $C_1$-$C_{20}$ (h+1)-valent fluorinated hydrocarbon group; $g^1$ is an integer of 1 to 3, $g^2$ is an integer satisfying $0 \leq g^2 \leq 5+2g^3-g^3$ is 0 or 1, and h is an integer of 1 to 3.

In a further aspect, the invention provides a resist pattern forming process comprising the steps of applying the resist composition defined above onto a substrate to form a resist film thereon, exposing the resist film patternwise to high-energy radiation, and developing the exposed resist film in an alkaline developer to form a resist pattern.

Typically, the high-energy radiation is EUV or EB.

In one embodiment, the substrate has an outermost surface of chromium-containing material. Typically, the substrate is a photomask blank.

Advantageous Effects of Invention

A chemically amplified positive resist composition comprising the onium salt defined herein as PAG exhibits a very high resolution when processed by the micropatterning lithography, especially EB and EUV lithography. A pattern with minimal LER is obtainable therefrom. A hole pattern of rectangular profile is obtainable.

DESCRIPTION OF PREFERRED EMBODIMENTS

As used herein, the singular forms "a," "an" and "the" include plural referents unless the context clearly dictates otherwise. "Optional" or "optionally" means that the subsequently described event or circumstance may or may not occur, and that description includes instances where the event or circumstance occurs and instances where it does not. The notation (Cn-Cm) means a group containing from n to m carbon atoms per group.

The abbreviations and acronyms have the following meaning.

PAG: photoacid generator
Mw: weight average molecular weight
Mn: number average molecular weight
Mw/Mn: molecular weight distribution or dispersity
GPC: gel permeation chromatography
PEB: post-exposure baking
PED: post-exposure delay
LER: line edge roughness
CDU: critical dimension uniformity It is understood that for some structures represented by chemical formulae, there can exist enantiomers and diastereomers because of the presence of asymmetric carbon atoms. In such a case, a single formula collectively represents all such isomers. The isomers may be used alone or in admixture. In chemical formulae, the broken line denotes a valence bond.

Onium Salt

One embodiment of the invention is an onium salt of arenesulfonic acid having a bridged ring-containing group, represented by the formula (1).

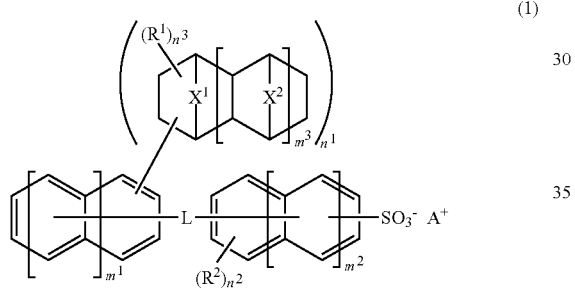

(1)

In formula (1), $X^1$ and $X^2$ are each independently a methylene group, propane-2,2-diyl group or ether bond.

L is a single bond, ester bond, sulfonic acid ester bond, carbonate bond or carbamate bond, with the ester bond or sulfonic acid ester bond being preferred.

$R^1$ and $R^2$ are each independently a $C_1$-$C_{20}$ monovalent hydrocarbon group which may contain a heteroatom. The monovalent hydrocarbon group may be straight, branched or cyclic. Examples include alkyl groups such as methyl, ethyl, propyl, isopropyl, n-butyl, sec-butyl, t-butyl, n-pentyl, t-pentyl, n-hexyl, n-octyl, n-nonyl, n-decyl; and monovalent saturated cycloaliphatic hydrocarbon groups such as cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl.

Preferably, $R^2$ is at the ortho-position relative to the —SO$_3$$^-$ group. This means that the —SO$_3$$^-$ group which is an acid function site is blocked by steric bulkiness. An apparent effect of controlling acid diffusion is exerted.

In formula (1), $m^1$ is an integer of 0 to 2, and $n^1$ is an integer satisfying $1 \leq n^1 \leq 5+2m^1$. From the aspect of dissolution control during development, $m^1$ is preferably 0 or 1, especially 0. For the purpose of introducing a substituent group into the salt to impart appropriate bulkiness to the acid generated therefrom upon exposure, $n^1$ is preferably an integer of 1 to 5, more preferably 1 to 3.

In formula (1), $m^2$ is an integer of 0 to 2, and $n^2$ is an integer satisfying $0 \leq n^2 \leq 4+2m^2$. Preferably, $m^2$ is 0 or 1, especially 0. For the purpose of introducing a substituent group into the salt to control the diffusion of the acid generated therefrom upon exposure, $n^2$ is preferably an integer of 0 to 4, more preferably 2 or 3.

In formula (1), $m^3$ is 0 or 1, and $n^3$ is an integer satisfying $0 \leq n^3 \leq 8+4m^3$. From the aspect of dissolution control during development, $m^3$ is preferably 0. From the aspect of dissolution control during development, $n^3$ is preferably an integer of 0 to 3, especially 0 or 1.

In formula (1), examples of the aromatic ring structure to which the bridged ring-containing group and L are attached include structures having the formulae (1-1) to (1-13), but are not limited thereto. Herein, the broken line designates a valence bond to L.

(1-1)

(1-2)

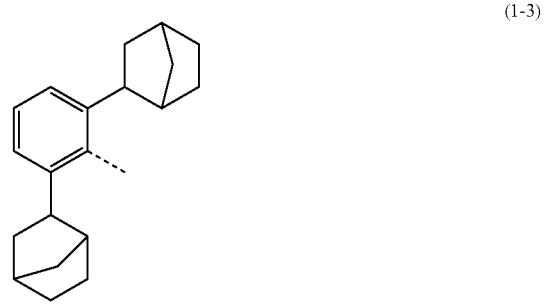

(1-3)

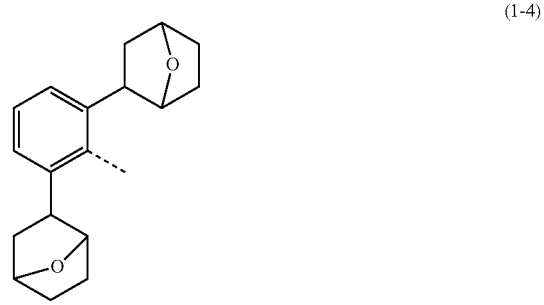

(1-4)

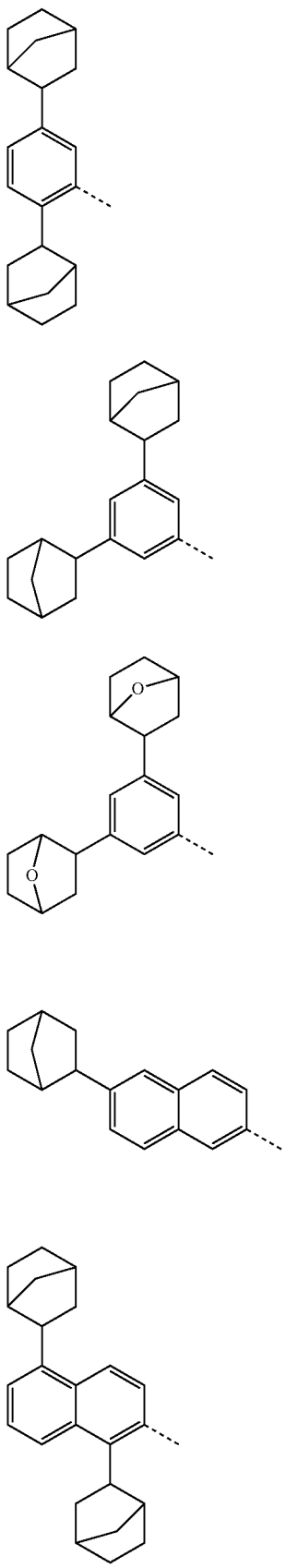
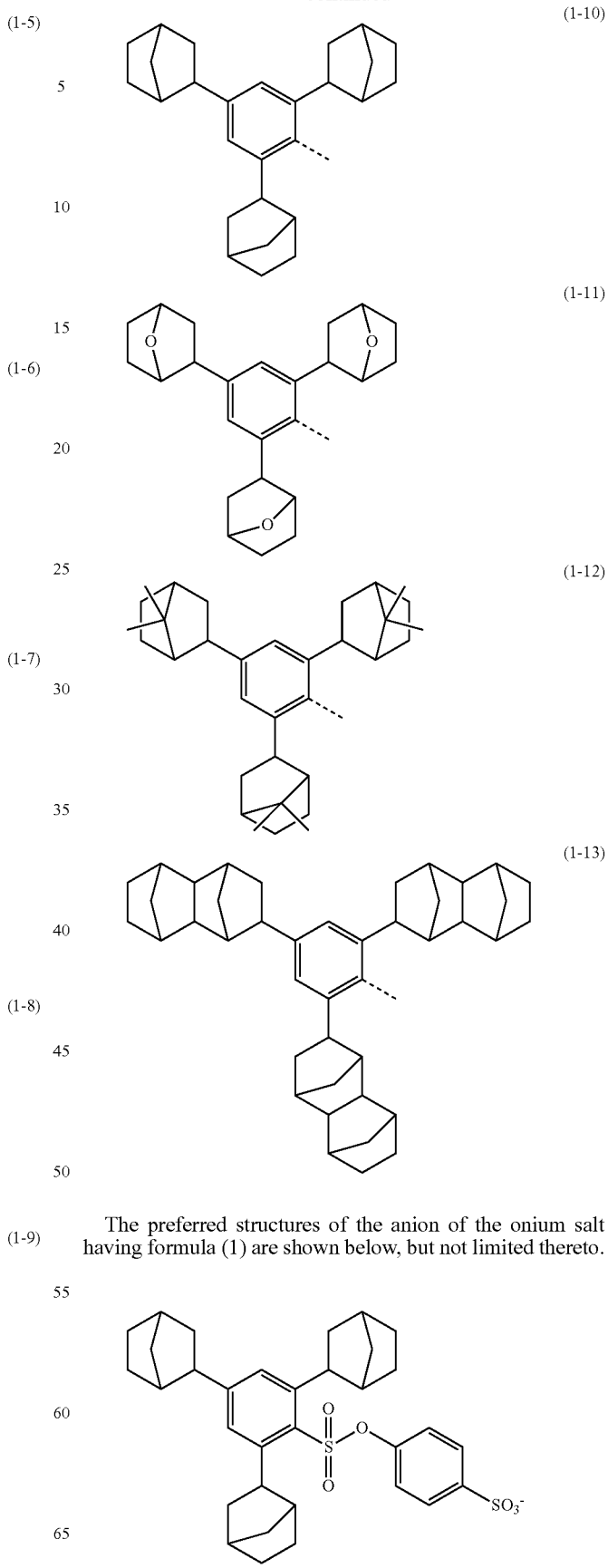
The preferred structures of the anion of the onium salt having formula (1) are shown below, but not limited thereto.

-continued
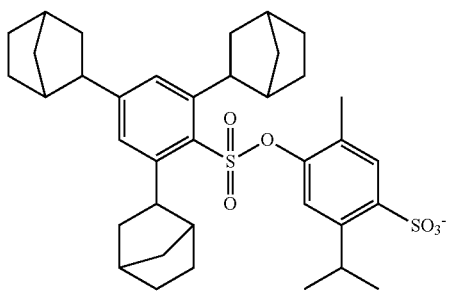
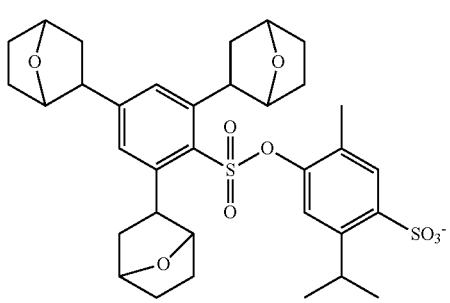
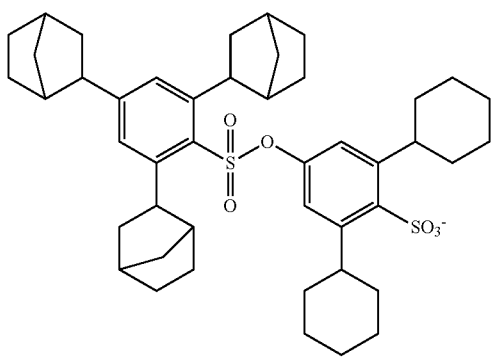
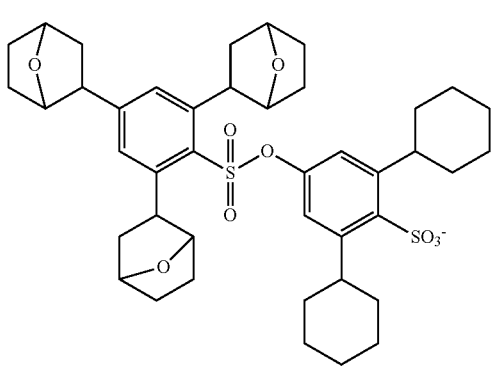
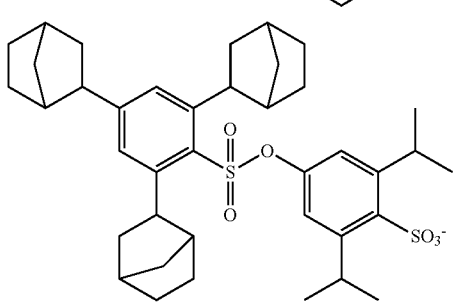
-continued
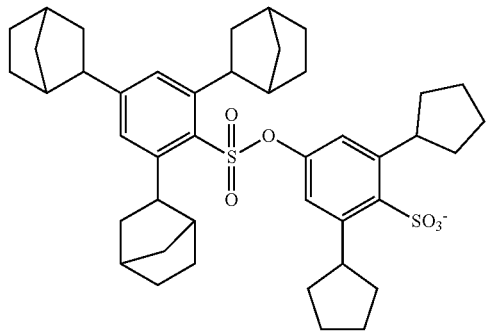
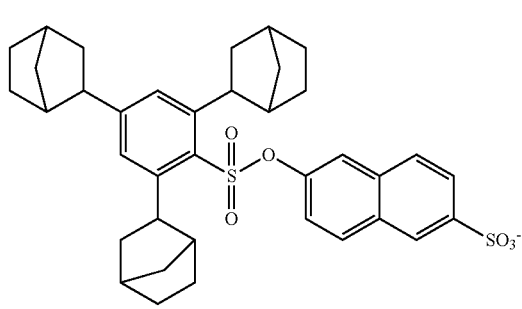
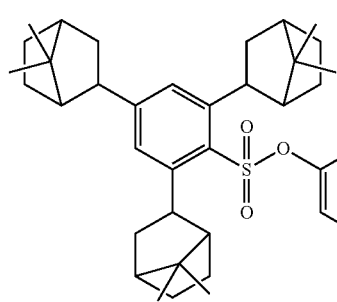

-continued

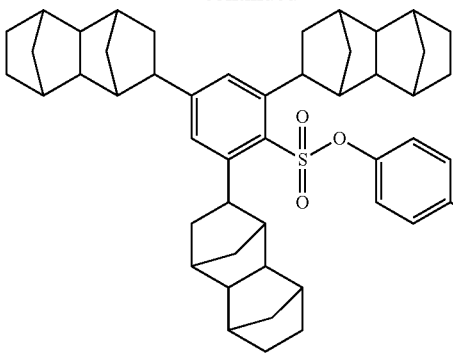
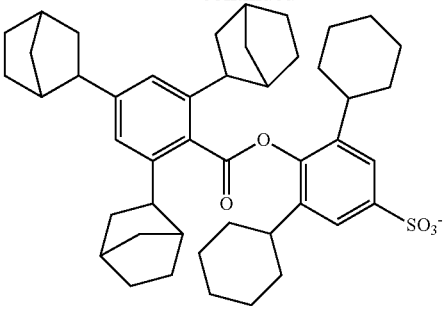
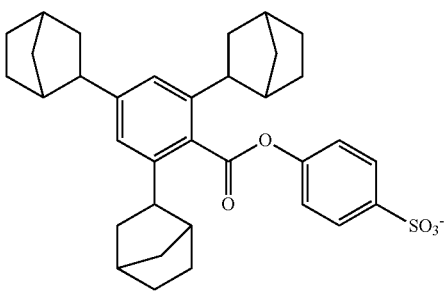
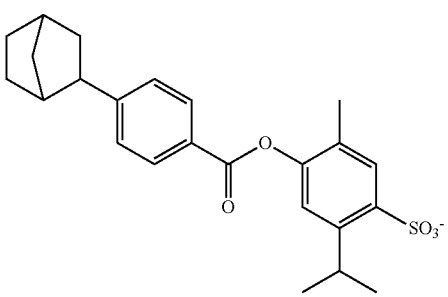
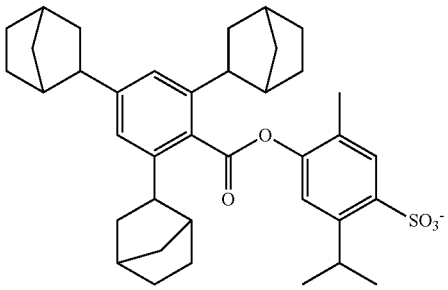

In formula (1), $A^-$ is a sulfonium cation having the formula (2), an iodonium cation having the formula (3), or an ammonium cation having the formula (4).

$$\begin{array}{c} R^{3A} \\ | \\ S^+ - R^{3B} \\ | \\ R^{3C} \end{array} \quad (2)$$

$$\begin{array}{c} R^{4A} \\ | \\ I^+ \\ | \\ R^{4B} \end{array} \quad (3)$$

$$\begin{array}{c} R^{5A} \\ | \\ R^{5D}-N^+-R^{5B} \\ | \\ R^{5C} \end{array} \quad (4)$$

In formulae (2) to (4), $R^{3A}$, $R^{3B}$, $R^{3C}$, $R^{4A}$, $R^{4B}$, $R^{5A}$, $R^{5B}$ and $R^{5C}$ are each independently a $C_1$-$C_{20}$ monovalent hydrocarbon group which may contain a heteroatom. $R^{5D}$ is hydrogen or a $C_1$-$C_{20}$ monovalent hydrocarbon group which may contain a heteroatom. Any two of $R^{3A}$, $R^{3B}$, and $R^{3C}$, or any two of $R^{5A}$, $R^{5B}$, $R^{5C}$, and $R^{5D}$ may bond together to form a ring with the sulfur or nitrogen atom to which they are attached.

The monovalent hydrocarbon group may be straight, branched or cyclic. Examples include alkyl groups such as methyl, ethyl, n-propyl, isopropyl, n-butyl, and t-butyl, monovalent saturated cycloaliphatic hydrocarbon groups such as cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, and hexenyl, monovalent unsaturated cycloaliphatic hydrocarbon groups such as cyclohexenyl, aryl groups such as phenyl and naphthyl, heteroaryl groups such as thienyl, and aralkyl groups such as benzyl, 1-phenylethyl and 2-phenylethyl. Inter alia, aryl groups are preferred. In these hydrocarbon groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride (—C(=O)—O—C(=O)—) or haloalkyl moiety.

In formula (2), any two of $R^{3A}$, $R^{3B}$, and $R^{3C}$ may bond together to form a ring with the sulfur atom to which they are attached. Examples of the sulfonium cation in this embodiment are shown below, but not limited thereto.
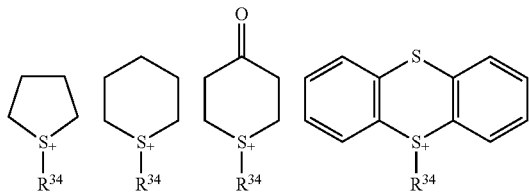
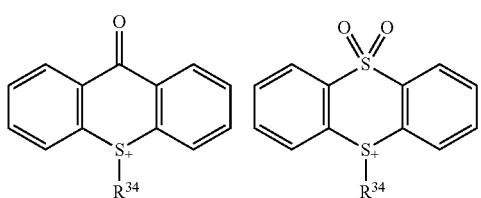
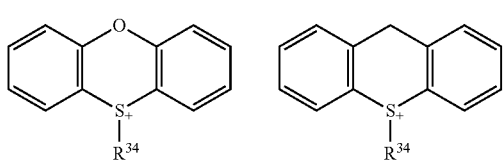
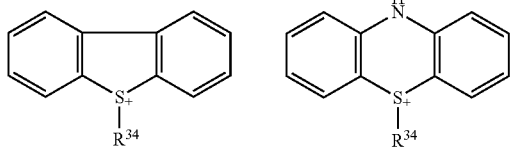
Herein $R^{3D}$ is the same as defined and exemplified for $R^{3A}$ to $R^{3C}$.
Examples of the sulfonium cation having formula (2) are shown below, but not limited thereto.
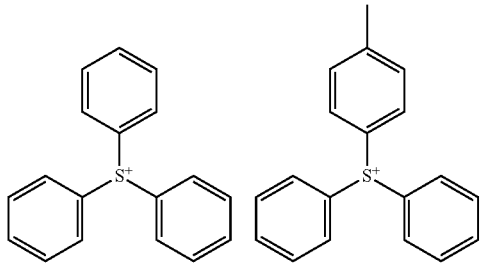
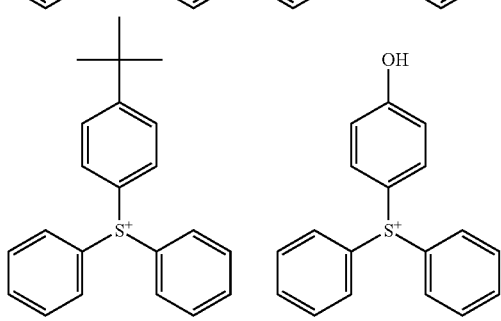
-continued
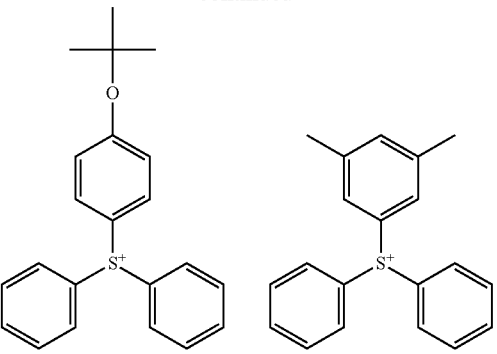
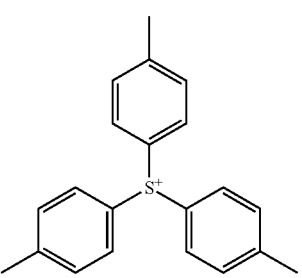
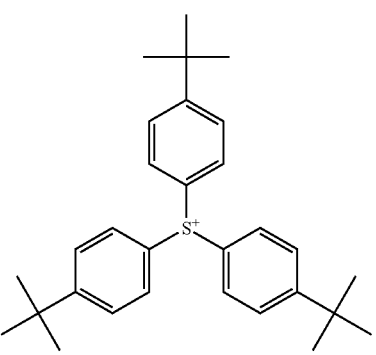
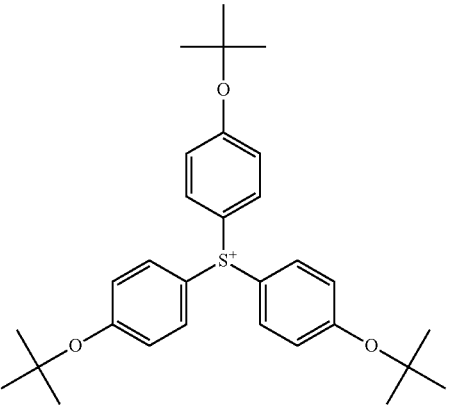
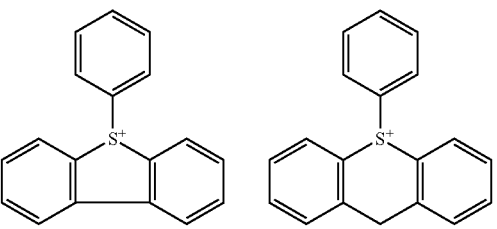

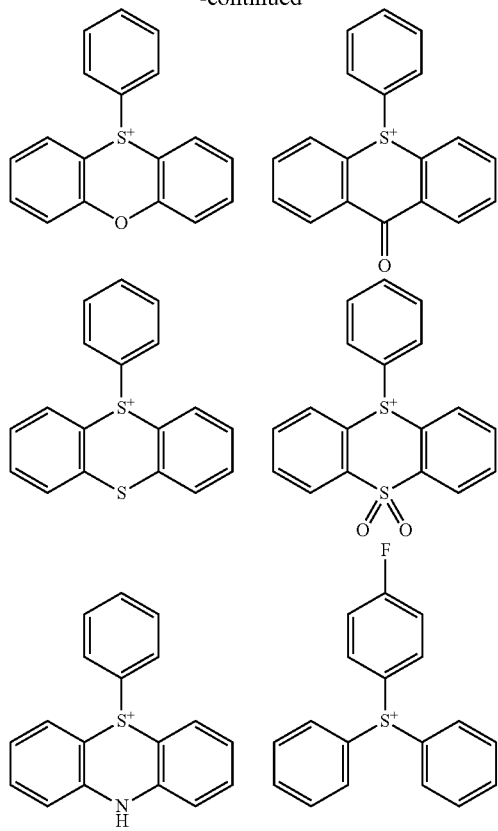

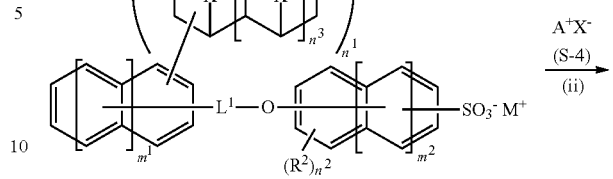

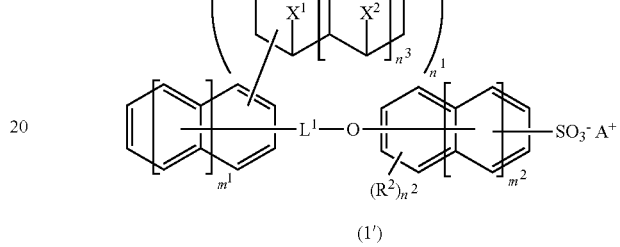

Examples of the iodonium cation having formula (3) include diphenyliodonium, bis(4-methylphenyl)iodonium, bis(4-(1,1-dimethylethyl)phenyl)iodonium, bis(4-(1,1-dimethylpropyl)phenyl)iodonium, and (4-(1,1-dimethylethoxy)phenyl)phenyliodonium cations.

Examples of the ammonium cation having formula (4) include tertiary ammonium cations such as trimethylammonium, triethylammonium, tributylammonium and N,N-dimethylanilinium cations and quaternary ammonium cations such as tetramethylammonium, tetraethylammonium and tetrabutylammonium cations.

Exemplary structures of the onium salt include arbitrary combinations of anions with cations, both as exemplified above.

The method for synthesizing the onium compound having formula (1), for example, formula (1) wherein L is an ester bond or sulfonic acid ester bond is exemplified by the following reaction scheme A, but not limited thereto.

Scheme A

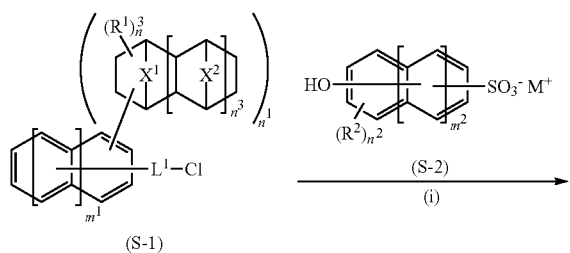

Herein $R^1$ to $R^5$, $X^1$, $X^2$, $A^+$, $m^1$ to $m^3$, $n^1$ to $n^3$ are as defined above, $L^1$ is a carbonyl or sulfonyl group, $M^+$ is a lithium, sodium or potassium ion, and $X^-$ is a halide or methyl sulfate ion.

Step (i) is nucleophilic displacement reaction of acid chloride (S-1) with hydroxyarene sulfonic acid salt (S-2) to form sulfonic acid salt (S-3). The reaction may be conducted by the standard technique, specifically by sequentially or simultaneously adding the acid chloride (S-1), the hydroxyarene sulfonic acid salt (S-2), and a base to a solvent and allowing the reaction to take place while cooling or heating if necessary.

Suitable solvents which can be used in step (i) include water; ethers such as tetrahydrofuran (THF), diethyl ether, diisopropyl ether, di-n-butyl ether and 1,4-dioxane; hydrocarbons such as n-hexane, n-heptane, benzene, toluene, and xylene; aprotic polar solvents such as acetonitrile, dimethyl sulfoxide (DMSO) and N,N-dimethylformamide (DMF); and chlorinated solvents such as methylene chloride, chloroform and carbon tetrachloride. The solvent may be selected depending on reaction conditions while it may be used alone or in admixture.

Suitable bases which can be used in step (i) include amines such as ammonia, triethylamine, pyridine, lutidine, collidine, and N,N-dimethylaniline; hydroxides such as sodium hydroxide, potassium hydroxide and tetramethylammonium hydroxide; and carbonates such as potassium carbonate and sodium hydrogencarbonate, which may be used alone or in admixture.

Step (ii) is ion exchange reaction between sulfonic acid salt (S-3) and onium salt (S-4) to form onium salt (1'). As the sulfonic acid salt (S-3), the reaction product resulting from step (i) may be used in crude form (after the termination of reaction and without post-treatment) or after it is isolated by customary aqueous work-up.

Where the isolated form of sulfonic acid salt (S-3) is used, a reaction mixture is obtained by dissolving the salt (S-3) in a solvent, mixing with onium salt (S-4), and optionally cooling or heating. Examples of the solvent used herein include water; ethers such as THF, diethyl ether, diisopropyl ether, di-n-butyl ether and 1,4-dioxane; hydrocarbons such as n-hexane, n-heptane, benzene, toluene, and xylene; aprotic polar solvents such as acetonitrile, DMSO and DMF; and chlorinated solvents such as methylene chloride, chloroform and carbon tetrachloride. From the reaction mixture, onium salt (1') may be recovered via customary aqueous work-up. If necessary, the salt may be purified by standard techniques like distillation, recrystallization and chromatography.

Where the crude form of sulfonic acid salt (S-3) is used, an onium salt (1') is obtained by adding onium salt (S-4) to the reaction mixture at the end of synthesis reaction (step i) of sulfonic acid salt (S-3) and optionally cooling or heating. If necessary, a solvent may be added to the reaction mixture. Examples of the solvent include water; ethers such as THF, diethyl ether, diisopropyl ether, di-n-butyl ether and 1,4-dioxane; hydrocarbons such as n-hexane, n-heptane, benzene, toluene, and xylene; aprotic polar solvents such as acetonitrile, DMSO and DMF; and chlorinated solvents such as methylene chloride, chloroform and carbon tetrachloride. From the reaction mixture, onium salt (1') may be recovered via customary aqueous work-up. If necessary, the salt may be purified by standard techniques like distillation, recrystallization and chromatography.

Since the onium salt of formula (1) has an onium salt structure of non-fluorinated sulfonic acid, it generates an acid with appropriate strength upon exposure to high-energy radiation. Since the onium salt has a bulky substituent group such as norbornyl or oxanorbornyl, the movement and diffusion of the generated acid can be appropriately controlled, contributing to roughness improvement. In particular, a hole pattern of rectangular profile is obtainable. Since the onium salt is fully lipophilic, it is easy to prepare and handle.

Resist Composition

Another embodiment of the invention is a chemically amplified positive resist composition comprising (A) an acid generator containing the onium salt of formula (1) and (B) a base polymer containing a polymer adapted to be decomposed under the action of acid to increase its solubility in alkaline developer.

(A) Acid Generator

The onium salt having formula (1) generates a sulfonic acid having the following formula (1a) in response to high-energy radiation or heat.

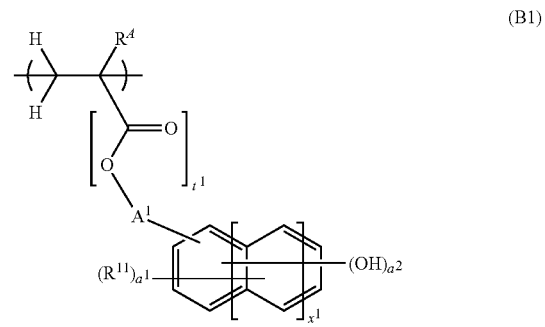

(1a)

Herein $R^1$, $R^2$, $X^1$, $X^2$, L, $m^1$ to $m^3$, $n^1$ to $n^3$ are as defined above.

The acid generator (A) may contain another acid generator other than the onium salt of formula (1). The other acid generator may be selected from prior art well-known acid generators, typically compounds capable of generating an acid in response to actinic light or radiation, known as photoacid generator (PAG). The PAG is any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. These PAGs may be used alone or in admixture.

In the resist composition, the acid generator (A) is preferably present in an amount of 0.1 to 40 parts by weight, more preferably 1 to 20 parts by weight per 100 parts by weight of the base polymer (B). When the amount of the acid generator falls in the range, a sufficient amount of acid to deprotect the acid labile group is generated and storage stability is satisfactory.

(B) Base Polymer

The positive resist composition also comprises (B) a base polymer containing a polymer adapted to be decomposed under the action of acid to increase its solubility in alkaline developer. The preferred polymer is a polymer comprising recurring units having the formula (B1). It is noted that the recurring unit having formula (B1) is simply referred to as recurring unit (B1).

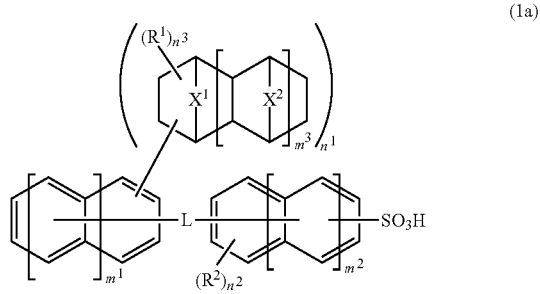

(B1)

In formula (B1), $R^A$ is hydrogen, fluorine, methyl or trifluoromethyl, with hydrogen or methyl being preferred. $R^{11}$ is each independently halogen, an optionally halogenated $C_2$-$C_8$ acyloxy group, optionally halogenated $C_1$-$C_6$ alkyl group, or optionally halogenated $C_1$-$C_6$ alkoxy group. $A^1$ is a single bond or $C_1$-$C_{10}$ alkanediyl group in which an ether bond may intervene in a carbon-carbon bond, $t^1$ is 0 or 1, $x^1$ is an integer of 0 to 2, $a^1$ is an integer satisfying $0 \leq a^1 \leq 5+2x^1-a^2$, and $a^2$ is an integer of 1 to 3.

Examples of the alkanediyl group $A^1$ include methylene, ethylene, propylene, butylene, pentylene, hexylene, and structural isomers of carbon skeleton having a branched or cyclic structure. Where the alkanediyl group contains an ether bond, in case of $t^1=1$ in formula (B1), the ether bond may take any position excluding the position between α-carbon and β-carbon relative to the ester oxygen. In case of $t^1=0$, the atom bonding with the backbone becomes an ethereal oxygen atom, and a second ether bond may take any position excluding the position between α-carbon and β-carbon relative to the ethereal oxygen atom. As long as the carbon count of the alkanediyl group is 10 or less, sufficient solubility in alkaline developer is available.

Preferred examples of the hydrocarbon moiety in the acyloxy, alkyl and alkoxy groups represented by $R^{11}$ include methyl, ethyl, propyl, isopropyl, butyl, pentyl, hexyl and structural isomers of carbon skeleton having a branched or cyclic structure. As long as the carbon count of the group is not more than the upper limit, sufficient solubility in alkaline developer is available.

In formula (B1), $x^1$ is an integer of 0 to 2. The relevant skeleton is a benzene skeleton in case of $x^1=0$, a naphthalene skeleton in case of $x^1=1$, and an anthracene skeleton in case of $x^1=2$. The subscript $a^1$ is an integer satisfying $0 \le a^1 \le 5+2x^1-a^2$. In case of $x^1=0$, preferably $a^1$ is an integer of 0 to 3 and $a^2$ is an integer of 1 to 3. In case of $x^1=1$ or 2, preferably $a^1$ is an integer of 0 to 4 and $a^2$ is an integer of 1 to 3.

Where the recurring units (B1) are free of a linker (—CO—O-$A^1$-), that is, have formula (B1) wherein $t^1=0$ and $A^1$ is a single bond, suitable recurring units (B1) include those derived from 3-hydroxystyrene, 4-hydroxystyrene, 5-hydroxy-2-vinylnaphthalene, and 6-hydroxy-2-vinylnaphthalene.

Where the recurring units (B1) have a linker (—CO—O-$A^1$-), that is, have formula (B1) wherein $t^1=1$, preferred examples of the recurring units (B1) are given below, but not limited thereto. Herein $R^4$ is as defined above.

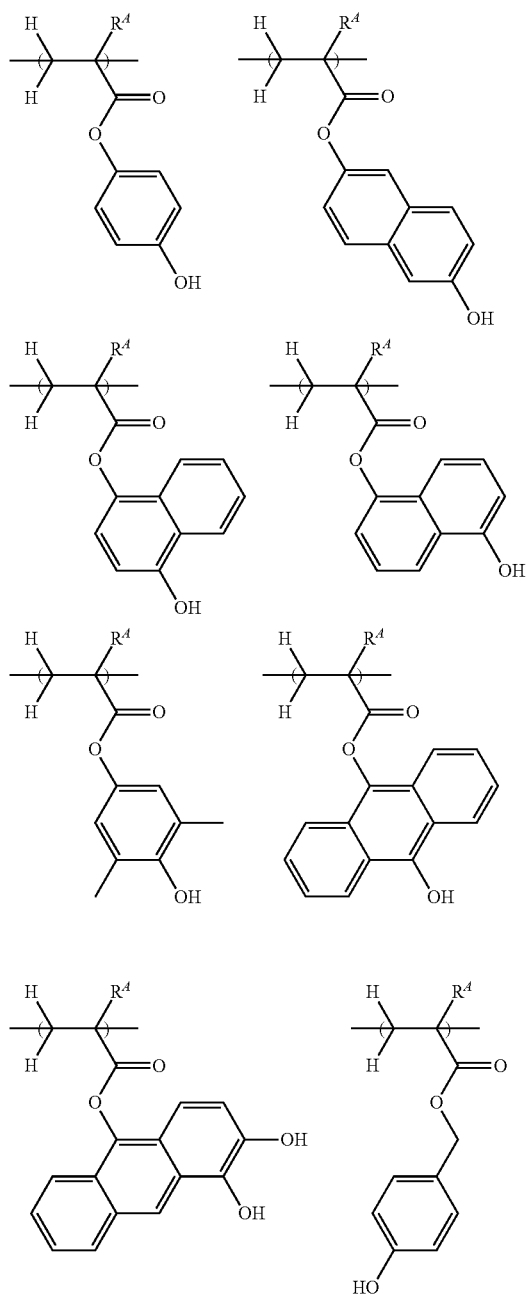

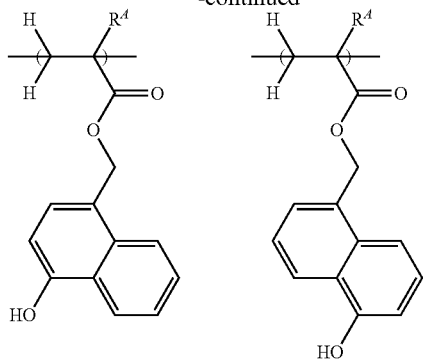

The recurring units (B1) may be of one type or a mixture of two or more types. The recurring units (B1) are incorporated in an amount of preferably 5 to 95 mol %, more preferably 20 to 80 mol %, based on the entire recurring units of the polymer.

In order that the resist composition serve as a positive resist composition wherein the exposed region of a resist film is dissolved in alkaline aqueous solution, the polymer should preferably further comprise units having an acidic functional group protected with an acid labile group, that is, units which are protected with an acid labile group, but turn alkali soluble under the action of acid, referred to as recurring units (B2), hereinafter.

Of the recurring units (B2), recurring units having the formula (B2) are most preferred.

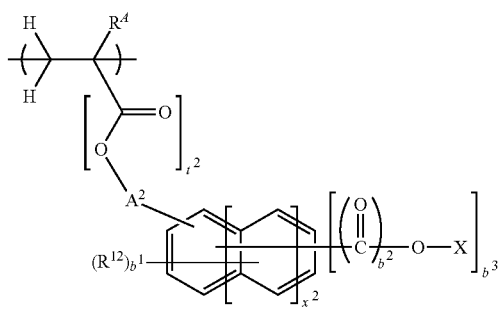

(B2)

In formula (B2), $R^4$ is as defined above. $R^{12}$ is each independently halogen, an optionally halogenated $C_2$-$C_8$ acyloxy group, optionally halogenated $C_1$-$C_6$ alkyl group, or optionally halogenated $C_1$-$C_6$ alkoxy group. $A^2$ is a single bond or $C_1$-$C_{10}$ alkanediyl group in which an ether bond may intervene in a carbon-carbon bond, $t^2$ is 0 or 1, $x^2$ is an integer of 0 to 2, $b^1$ is an integer satisfying $0 \le b1 \le 5+2x^2-b^3$, $b^2$ is 0 or 1, and $b^3$ is an integer of 1 to 3. When $b^3$ is 1, X is an acid labile group. When $b^3$ is 2 or 3, X is each independently hydrogen or an acid labile group, at least one X being an acid labile group.

Examples of the alkanediyl group $A^2$ include methylene, ethylene, propylene, butylene, pentylene, hexylene, and structural isomers of carbon skeleton having a branched or cyclic structure. Where the alkanediyl group contains an ether bond, in case of $t^2=1$ in formula (B2), the ether bond may take any position excluding the position between α-carbon and β-carbon relative to the ester oxygen. In case of $t^2=0$, the atom bonding with the backbone becomes an ethereal oxygen atom, and a second ether bond may take any position excluding the position between α-carbon and β-carbon relative to the ethereal oxygen atom. As long as the carbon count of the alkanediyl group is 10 or less, sufficient solubility in alkaline developer is available.

Preferred examples of the hydrocarbon moiety in the acyloxy, alkyl and alkoxy groups represented by $R^{12}$ include methyl, ethyl, propyl, isopropyl, butyl, pentyl, hexyl and structural isomers of carbon skeleton having a branched or cyclic structure. As long as the carbon count of the group is not more than the upper limit, sufficient solubility in alkaline developer is available.

In formula (B2), $x^2$ is an integer of 0 to 2. The relevant skeleton is a benzene skeleton in case of $x^2=0$, a naphthalene skeleton in case of $x^2=1$, and an anthracene skeleton in case of $x^2=2$. The subscript $b^1$ is an integer satisfying $0 \leq b^1 \leq 5 + 2x^2 - b^3$. In case of $x^2=0$, preferably $b^1$ is an integer of 0 to 3. In case of $x^2=1$ or 2, preferably $b^1$ is an integer of 0 to 4.

The recurring unit (B2) is the unit in which at least one of phenolic hydroxyl groups attached to aromatic ring is protected with an acid labile group, or a carboxyl group attached to aromatic ring is protected with an acid labile group. The acid labile group used herein is not particularly limited. It may be any of acid labile groups which are commonly used in many well-known chemically amplified resist compositions as long as it is eliminated with an acid to provide an acidic group.

The acid labile group is typically selected from tertiary alkyl groups and acetal groups. Of the tertiary alkyl groups, those of 4 to 18 carbon atoms are preferred because a corresponding monomer subject to polymerization may be recovered by distillation.

In the tertiary alkyl group, suitable alkyl substituents on tertiary carbon are $C_1$-$C_{15}$ alkyl groups. The $C_1$-$C_{15}$ alkyl groups may be straight, branched or cyclic, an oxygen-containing functional group such as ether bond or carbonyl may intervene between carbon atoms. Also, the alkyl substituents on tertiary carbon may bond together to form a ring with the tertiary carbon.

Examples of the alkyl substituent include methyl, ethyl, propyl, adamantyl, norbornyl, tetrahydrofuran-2-yl, 7-oxanorbornan-2-yl, cyclopentyl, 2-tetrahydrofuryl, tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, tetracyclo[4.4.0.1$^{2,5}$.1$^{7,10}$]dodecyl, and 3-oxo-1-cyclohexyl.

Suitable tertiary alkyl groups include, but are not limited to, t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

Also, a group of the formula (B2-1) is often used as the acid labile group. It is a good choice of the acid labile group that ensures to form a pattern having a substantially rectangular pattern-substrate interface in a consistent manner. An acetal structure is formed when X is a group of formula (B2-1).

(B2-1)

In formula (B2-1), $R^{L1}$ is hydrogen or a $C_1$-$C_{10}$ monovalent saturated aliphatic hydrocarbon group which may be straight, branched or cyclic. A choice of $R^{L1}$ may depend on the designed sensitivity of acid labile group to acid. For example, hydrogen is selected when the acid labile group is designed to ensure relatively high stability and to be decomposed with strong acid. A straight alkyl group is selected when the acid labile group is designed to have relatively high reactivity and high sensitivity to pH changes. Although the choice varies with a particular combination of acid generator and quencher in the resist composition, $R^{L1}$ is preferably a group in which the carbon in bond with acetal carbon is secondary, when $R^{L2}$ is a relatively large alkyl group substituted at the end and the acid labile group is designed to undergo a substantial change of solubility by decomposition. Examples of $R^{L1}$ bonded to acetal carbon via secondary carbon include isopropyl, sec-butyl, cyclopentyl, and cyclohexyl.

In formula (B2-1), $R^{L2}$ is a $C_1$-$C_{30}$ monovalent saturated aliphatic hydrocarbon group. For a higher resolution, $R^{L2}$ is preferably a $C_7$-$C_{30}$ polycyclic monovalent saturated aliphatic hydrocarbon group. When $R^{L2}$ is a polycyclic monovalent saturated aliphatic hydrocarbon group, a bond is preferably formed between secondary carbon on the polycyclic structure and acetal oxygen. The acetal oxygen bonded to secondary carbon on the cyclic structure, as compared with the acetal oxygen bonded to tertiary carbon on the cyclic structure, ensures that a corresponding polymer becomes a stable compound, suggesting that the resist composition has better shelf stability and is not degraded in resolution. Said acetal oxygen, as compared with $R^{L2}$ bonded to primary carbon via a straight alkanediyl group of at least one carbon atom, ensures that a corresponding polymer has a higher glass transition temperature (Tg), suggesting that a resist pattern after development is not deformed by bake.

Preferred examples of the group having formula (B2-1) are given below, but not limited thereto. Herein $R^{L1}$ is as defined above.

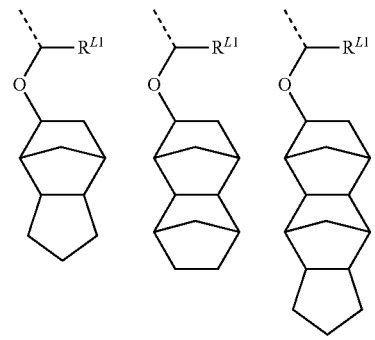

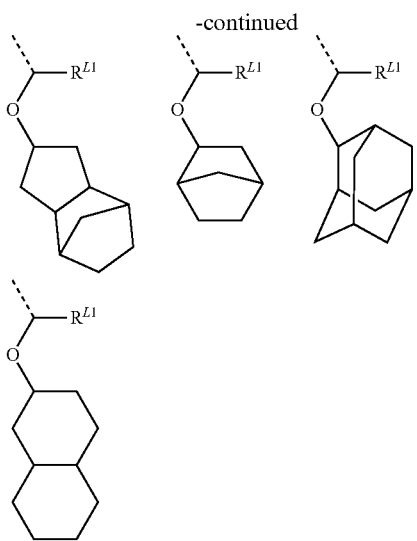

Another choice of acid labile group is a phenolic hydroxyl group having hydrogen substituted by —CH$_2$COO-(tertiary alkyl). The tertiary alkyl group used herein may be the same as the aforementioned tertiary alkyl groups used for the protection of phenolic hydroxyl group.

The recurring units (B2) may be of one type or a mixture of two or more types. In the polymer, the recurring units (B2) are preferably incorporated in a range of 5 to 95 mol %, more preferably 20 to 80 mol % based on the overall recurring units.

In a preferred embodiment, the polymer further comprises recurring units of at least one type selected from units of the formulae (B3), (B4) and (B5). These recurring units are simply referred to as recurring units (B3), (B4) and (B5), respectively.

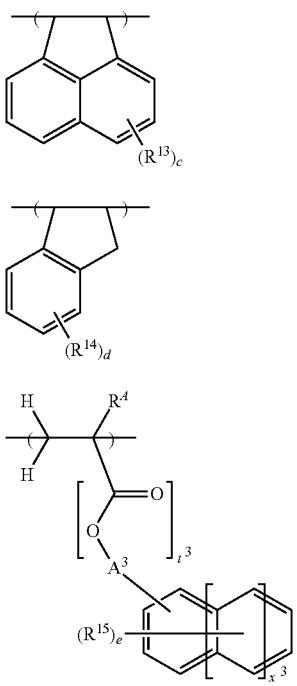

Herein $R^4$ is as defined above. $R^{13}$ and $R^{14}$ are each independently a hydroxyl group, halogen atom, acetoxy group, optionally halogenated $C_1$-$C_6$ alkyl group, optionally halogenated $C_1$-$C_6$ primary alkoxy group, optionally halogenated $C_2$-$C_6$ secondary alkoxy group, optionally halogenated $C_2$-$C_8$ acyloxy group, or optionally halogenated $C_2$-$C_8$ alkylcarbonyloxy group. $R^{15}$ is an acetyl group, acetoxy group, $C_1$-$C_{20}$ alkyl group, $C_1$-$C_{20}$ primary alkoxy group, $C_2$-$C_{20}$ secondary alkoxy group, $C_2$-$C_{20}$ acyloxy group, $C_2$-$C_{20}$ alkoxyalkyl group, $C_2$-$C_{20}$ alkylthioalkyl group, halogen atom, nitro group, or cyano group. $A^3$ is a single bond or $C_1$-$C_{10}$ alkanediyl group in which an ether bond may intervene in a carbon-carbon bond, c is an integer of 0 to 6, d is an integer of 0 to 4, e is an integer of 0 to 5, $t^3$ is 0 or 1, and $x^3$ is an integer of 0 to 2.

Examples of the alkanediyl group $A^3$ include methylene, ethylene, propylene, butylene, pentylene, hexylene, and structural isomers of carbon skeleton having a branched or cyclic structure. Where the alkanediyl group contains an ether bond, in case of $t^3$=1 in formula (B5), the ether bond may take any position excluding the position between α-carbon and β-carbon relative to the ester oxygen. In case of $t^3$=0, the atom bonding with the backbone becomes an ethereal oxygen atom, and a second ether bond may take any position excluding the position between α-carbon and β-carbon relative to the ethereal oxygen atom. As long as the carbon count of the alkanediyl group is 10 or less, sufficient solubility in alkaline developer is available.

Preferred examples of the hydrocarbon moiety in the alkyl, alkoxy, acyloxy, and alkylcarbonyloxy groups represented by $R^{13}$ and $R^{14}$ include methyl, ethyl, propyl, isopropyl, butyl, pentyl, hexyl and structural isomers of carbon skeleton having a branched or cyclic structure. As long as the carbon count of the group is not more than the upper limit, sufficient solubility in alkaline developer is available.

$R^{15}$ is preferably selected from chlorine, bromine, iodine, methyl, ethyl, propyl, butyl, pentyl, hexyl and structural isomers thereof, cyclopentyl, cyclohexyl, methoxy, ethoxy, propoxy, butoxy, pentyloxy, hexyloxy and structural isomers of their hydrocarbon moiety, cyclopentyloxy, and cyclohexyloxy. Inter alia, methoxy and ethoxy are useful. Also, an acyloxy group may be introduced into a polymer even at the end of polymerization by the chemical modification method and is thus advantageously used for fine adjustment of solubility of a base polymer in alkaline developer. Suitable acyloxy groups include methylcarbonyloxy, ethylcarbonyloxy, propylcarbonyloxy, butylcarbonyloxy, pentylcarbonyloxy, hexylcarbonyloxy and structural isomers thereof, cyclopentylcarbonyloxy, cyclohexylcarbonyloxy, and benzoyloxy groups. As long as the carbon count is not more than 20, the group is effective for appropriately controlling and adjusting (typically reducing) the solubility of a base polymer in alkaline developer and for preventing scum or development defects from forming. Of the preferred substituent groups mentioned above, chlorine, bromine, iodine, methyl, ethyl, and methoxy are especially useful because corresponding monomers are readily furnished.

In formula (B5), $x^3$ is an integer of 0 to 2. The relevant skeleton is a benzene skeleton in case of $x^3$=0, a naphthalene skeleton in case of $x^3$=1, and an anthracene skeleton in case of $x^3$=2. In case of $x^3$=0, preferably e is an integer of 0 to 3. In case of $x^3$=1 or 2, preferably e is an integer of 0 to 4.

Where the recurring units (B5) are free of a linker (—CO—O—$A^3$-), that is, have formula (B5) wherein $t^3$=0 and $A^3$ is a single bond, suitable recurring units (B5) include those derived from styrene, 4-chlorostyrene, 4-methylstyrene, 4-methoxystyrene, 4-bromostyrene, 4-acetoxystyrene, 2-hydroxypropylstyrene, 2-vinylnaphthalene, and 3-vinylnaphthalene.
Where the recurring units (B5) have a linker (—CO—O—$A^3$-), that is, have formula (B5) wherein $t^3$=1, preferred examples of the recurring units (B5) are given below, but not limited thereto. Herein $R^A$ is as defined above.
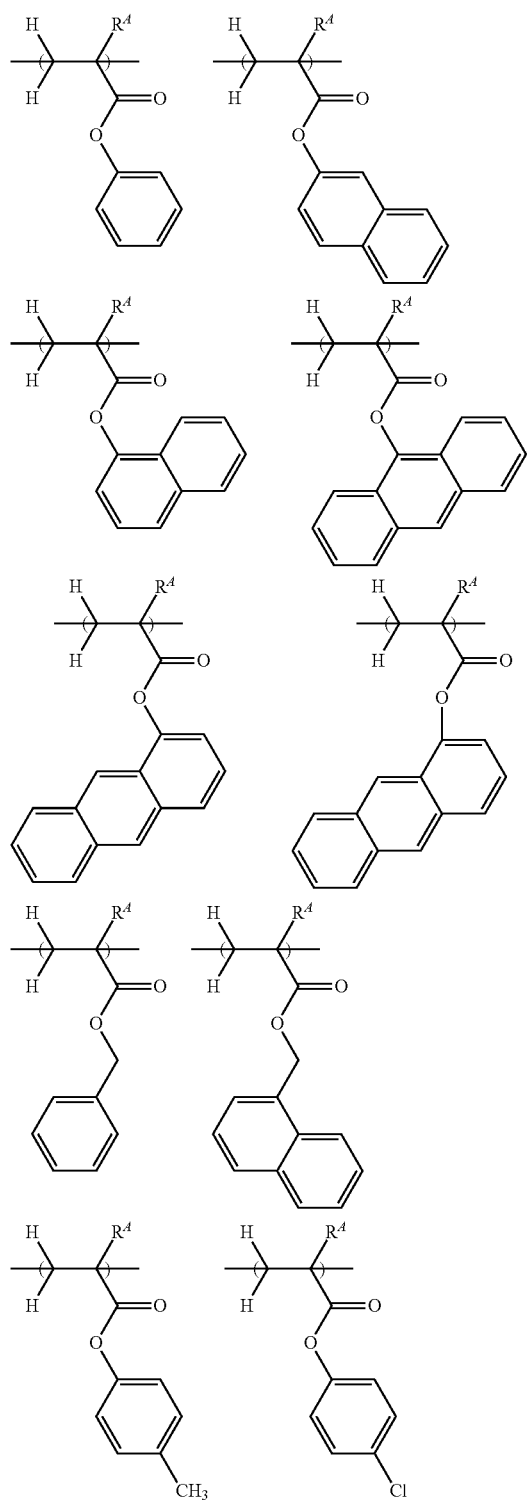
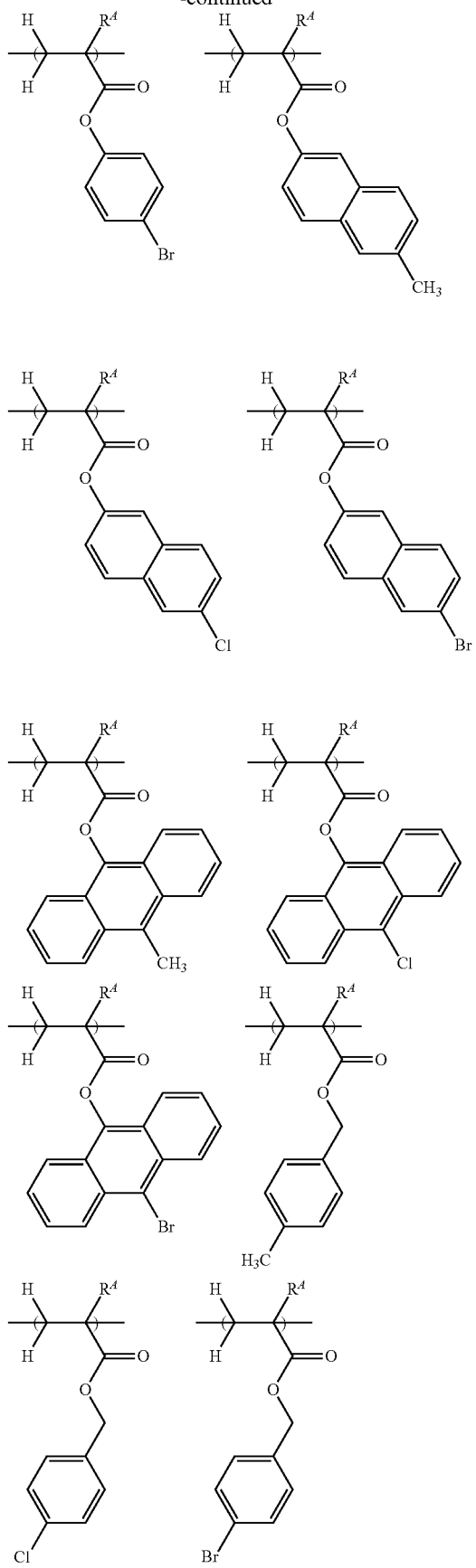

-continued

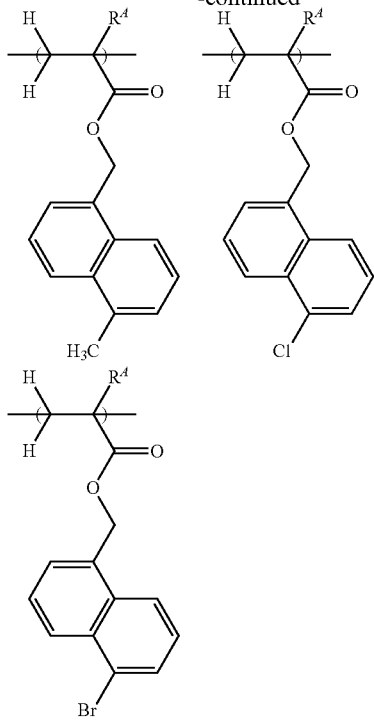

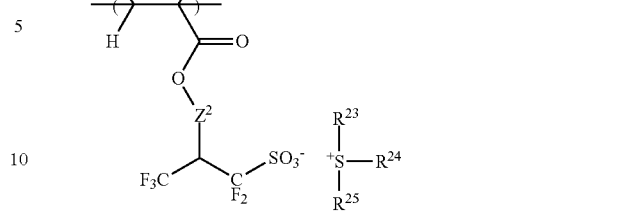

(B7)

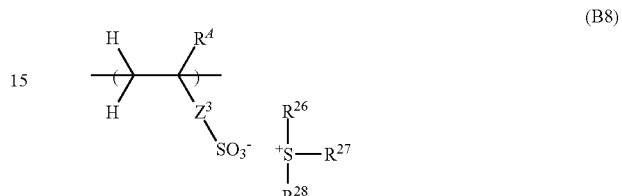

(B8)

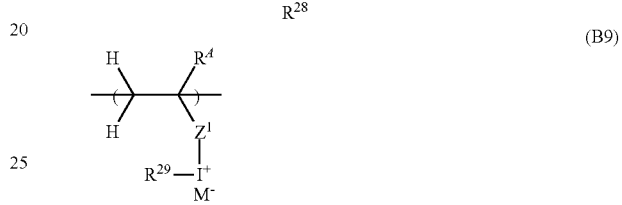

(B9)

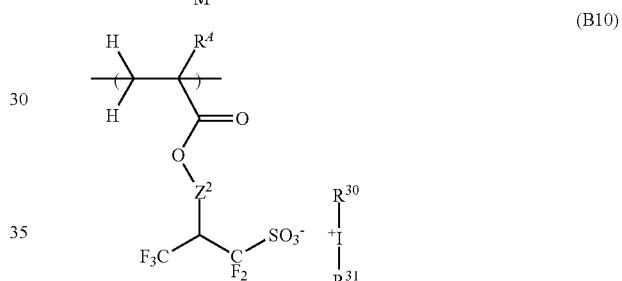

(B10)

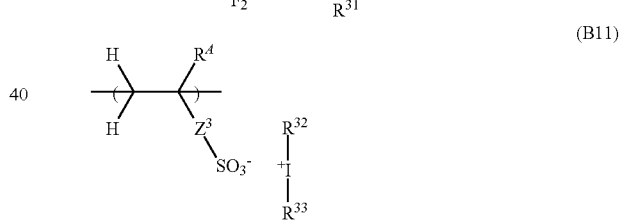

(B11)

When recurring units of at least one type selected from recurring units (B3) to (B5) are incorporated, better performance is obtained because not only the aromatic ring possesses etching resistance, but the cyclic structure incorporated into the main chain also exerts the effect of improving resistance to EB irradiation during etching and pattern inspection steps.

The recurring units (B3) to (B5) may be of one type or a combination of plural types. The total content of recurring units (B3) to (B5) is 0 to 45 mol % based on the overall recurring units of the polymer. From the aspect of improving etching resistance, the total content is preferably 2 to 45 mol %, more preferably 5 to 35 mol % based on the overall recurring units of the polymer.

The preferred polymer contains recurring units (B1), recurring units (B2), and recurring units of at least one type selected from recurring units (B3) to (B5) because both etch resistance and resolution are improved. These recurring units are preferably incorporated in an amount of at least 60 mol %, more preferably at least 70 mol %, even more preferably at least 80 mol %, based on the overall recurring units of the polymer.

The polymer may further comprise recurring units of at least one type selected from recurring units having formulae (B6) to (B11). Notably these recurring units are also referred to as recurring units (B6) to (B11).

(B6)

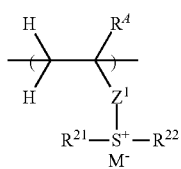

In formulae (B6) to (B11), $R^A$ is as defined above. $Z^1$ is each independently a single bond, phenylene group, —O—$Z^{11}$—, —C(=O)—O—$Z^{11}$— or —C(=O)—NH—$Z^{11}$—, wherein $Z^{11}$ is a $C_1$-$C_6$ alkanediyl, $C_2$-$C_6$ alkenediyl or phenylene group, which may contain a carbonyl, ester bond, ether bond or hydroxyl moiety. $Z^2$ is each independently a single bond or —$Z^{21}$—C(=O)—O—, wherein $Z^{21}$ is a $C_1$-$C_{20}$ divalent hydrocarbon group which may contain a heteroatom. $Z^3$ is each independently a single bond, methylene, ethylene, phenylene, fluorinated phenylene, —O—$Z^{31}$—, —C(=O)—O—$Z^{31}$—, or —C(=O)—NH—$Z^{31}$—, wherein $Z^{31}$ is a $C_1$-$C_6$ alkanediyl, $C_2$-$C_6$ alkenediyl or phenylene group, which may contain a carbonyl, ester bond, ether bond or hydroxyl moiety.

$R^{21}$ to $R^{33}$ are each independently a $C_1$-$C_{20}$ monovalent hydrocarbon group which may contain a heteroatom. In the hydrocarbon group, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride (—C(=O)—O—C(=O)—) or haloalkyl moiety. $R^{21}$ and $R^{22}$ may bond together to form a ring with the sulfur atom to which they are attached, any two of $R^{23}$, $R^{24}$ and $R^{25}$ may bond together to form a ring with the sulfur atom to which they are attached, and any two of $R^{26}$, $R^{27}$ and $R^{28}$ may bond together to form a ring with the sulfur atom to which they are attached. M$^-$ is a non-nucleophilic counter ion.

In formulae (B7) and (B10) wherein $Z^2$ is —$Z^{21}$—C(=O)—O—, $Z^{21}$ is a divalent hydrocarbon group which may contain a heteroatom-containing moiety. Illustrative, non-limiting examples of the hydrocarbon group $Z^{21}$ are given below.

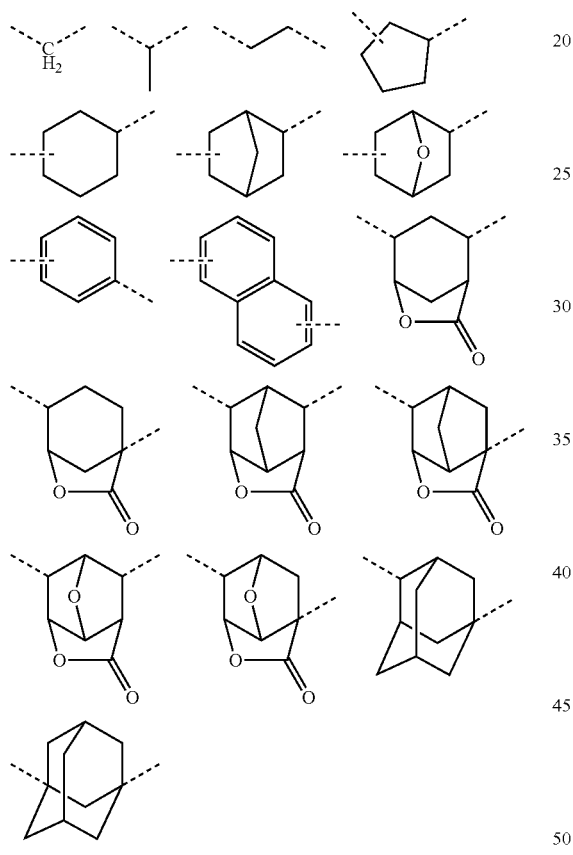

Illustrative, non-limiting examples of the sulfonium cation in formulae (B7) and (B8) wherein any two of $R^{23}$, $R^{24}$ and $R^{25}$, or any two of $R^{26}$, $R^{27}$ and $R^{28}$ bond together to form a ring with the sulfur atom to which they are attached, are shown below.

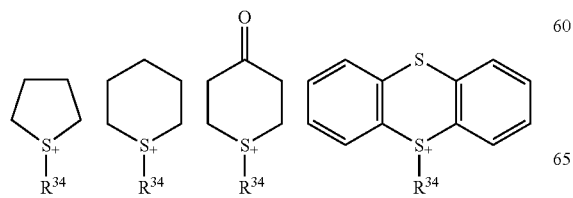

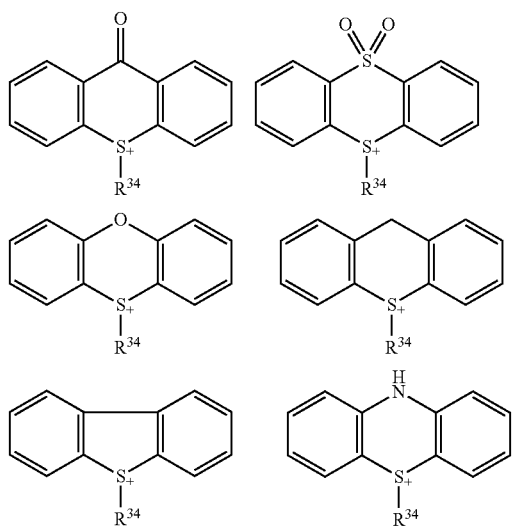

It is noted that $R^{34}$ is the same as defined and exemplified for $R^{21}$ to $R^{33}$.

Exemplary structures of the sulfonium cation in formulae (B7) and (B8) are shown below, but not limited thereto.

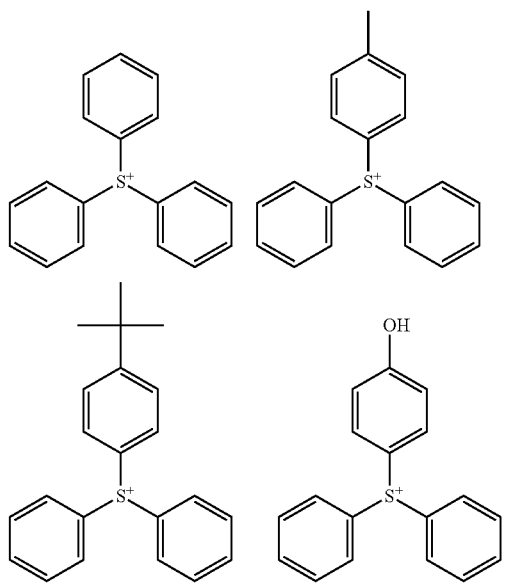

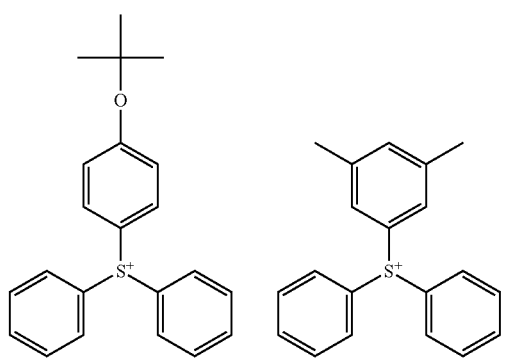

-continued
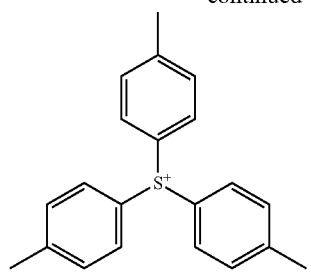
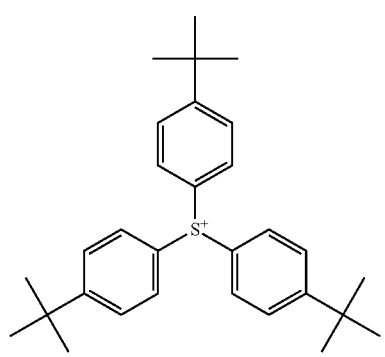
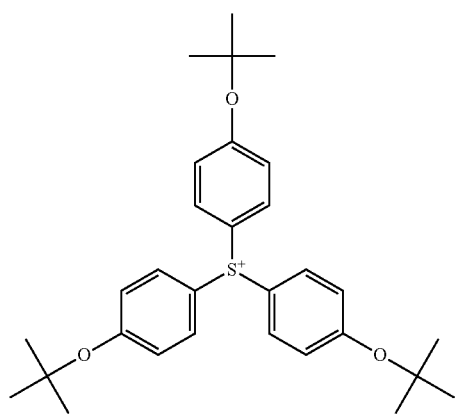
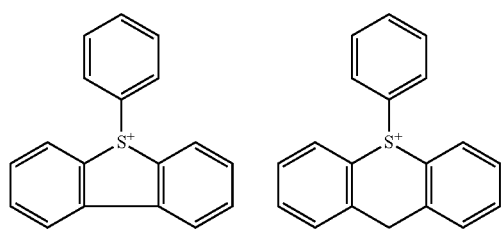
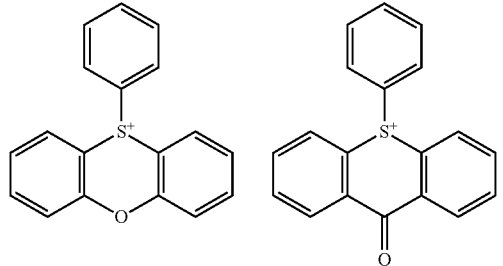
-continued
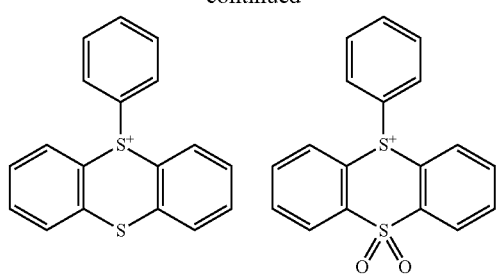
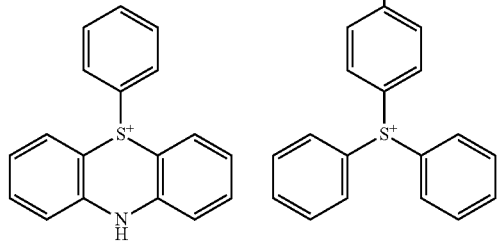
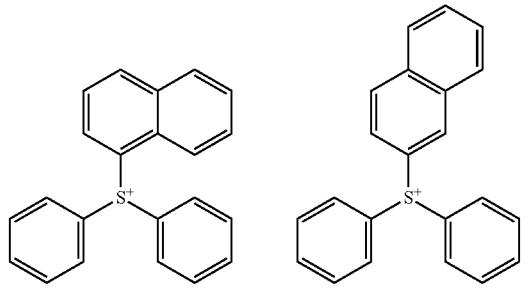
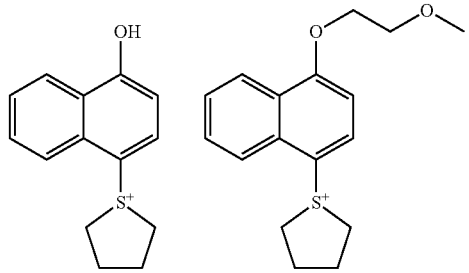
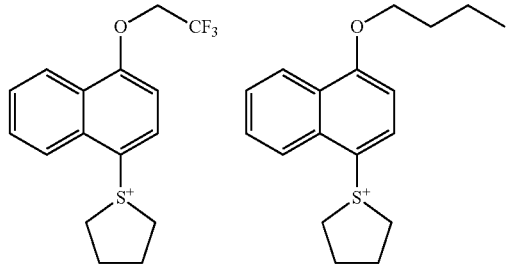
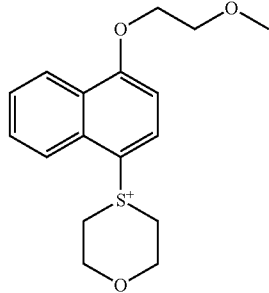

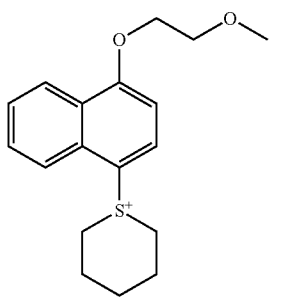
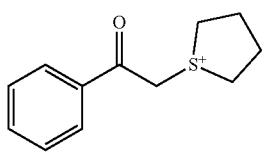
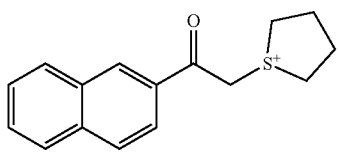
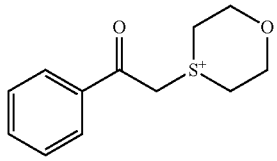
Exemplary structures of the iodonium cation in formulae (B10) and (B11) are shown below, but not limited thereto.
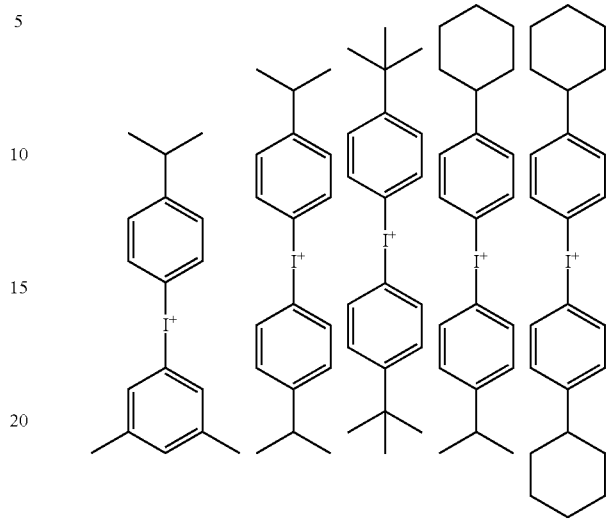
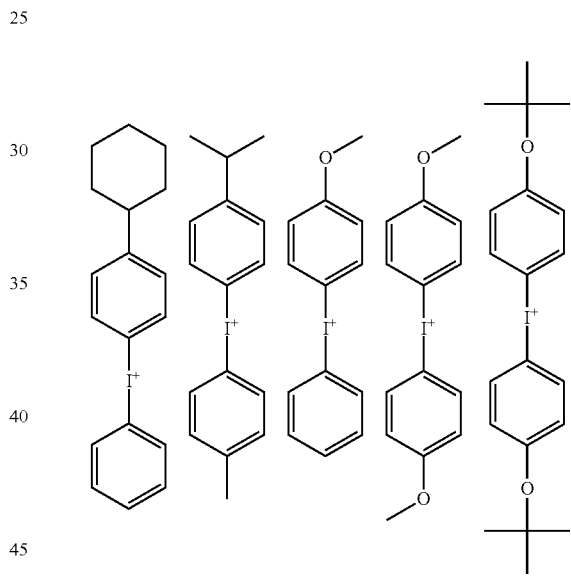
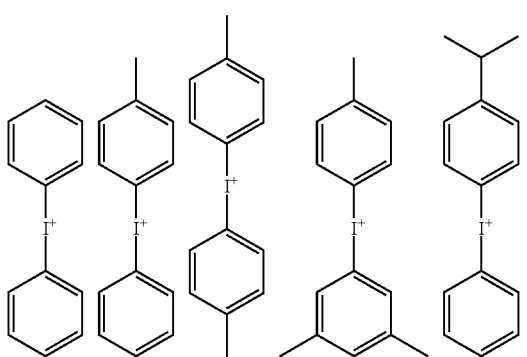
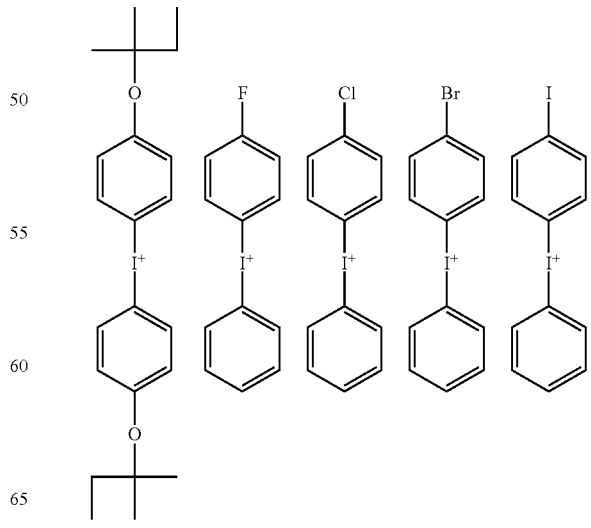

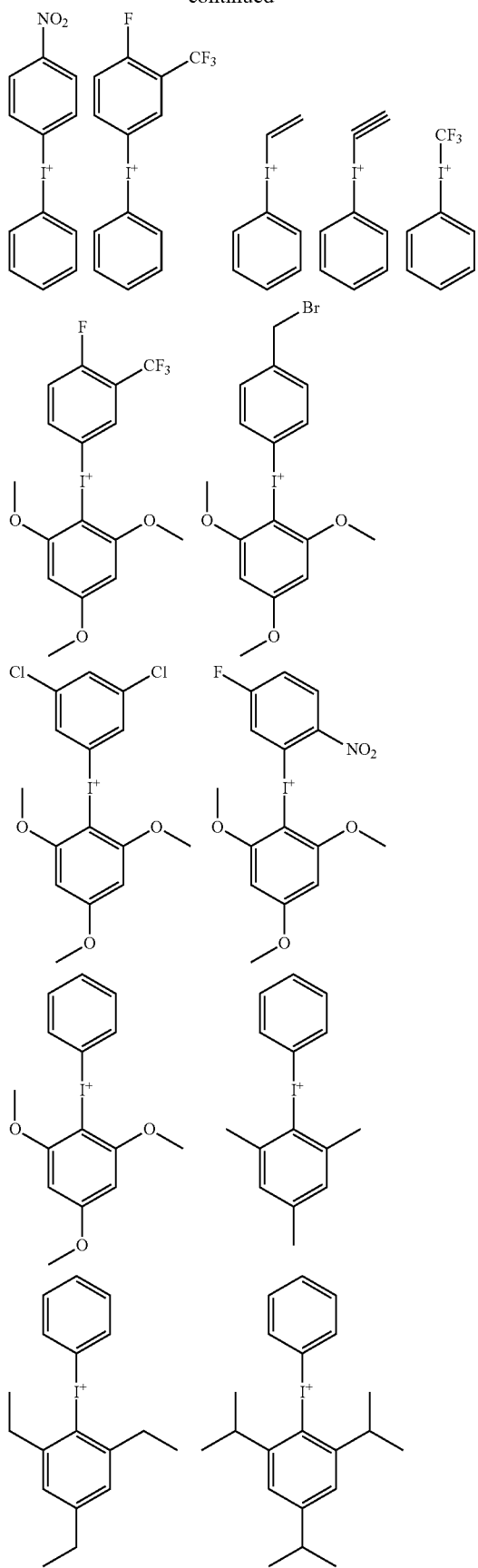
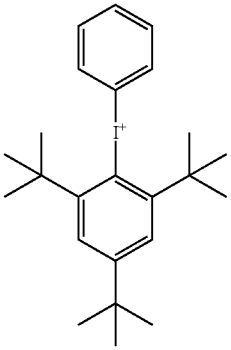
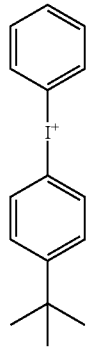

The recurring units (B6) to (B11) are units capable of generating an acid upon receipt of high-energy radiation. With the relevant units bound into a polymer, an appropriate control of acid diffusion becomes possible, and a pattern with minimal LER can be formed. Since the acid-generating unit is bound to a polymer, the chemical flare phenomenon that acid volatilizes from the exposed region and re-deposits on the unexposed region during bake in vacuum is suppressed. This is effective for reducing LER and for suppressing unwanted positive-toning reaction in the unexposed region for thereby reducing defects.

The total content of recurring units (B6) to (B11) is 0 to 30 mol %, and if incorporated, preferably 0.5 to 30 mol %, more preferably 1 to 25 mol % based on the overall recurring units of the polymer.

When the polymer contains recurring units (B1), recurring units (B2), and recurring units of at least one type selected from recurring units (B3) to (B5) and recurring units (B6) to (B11), the total content of these recurring units is preferably at least 60 mol %, more preferably at least 70 mol %, even more preferably at least 85 mol %, based on the overall recurring units of the polymer. The range ensures that the resist composition performs properly.

The polymer may further contain (meth)acrylate units protected with an acid labile group as commonly used, and/or (meth)acrylate units having an adhesive group such as lactone structure. These units may be incorporated for fine adjustment of properties of a resist film, though they are optional. When incorporated, these recurring units are used in an amount of preferably 0 to 30 mol %, more preferably 0 to 20 mol % of the overall recurring units of the polymer.

Examples of the (meth)acrylate units having an adhesive group include units having the formulae (B12) to (B14):

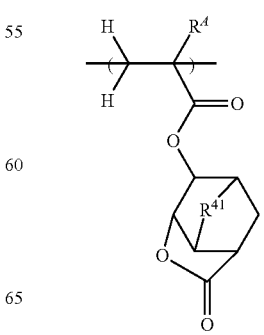

(B12)

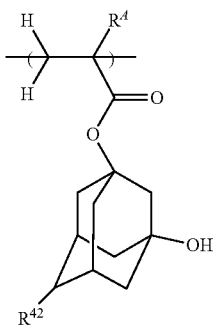

(B13)

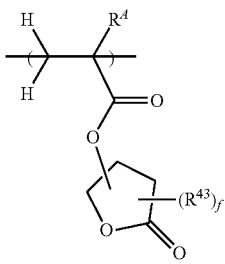

(B14)

wherein $R^A$ is as defined above, $R^{41}$ is —O— or methylene, $R^{42}$ is hydrogen or hydroxyl, $R^{43}$ is a $C_1$-$C_4$ alkyl group, and f is an integer of 0 to 3. These units do not exhibit acidity and may be used as supplemental units for imparting adhesion to substrates or for adjusting solubility.

The polymer may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to JP-A 2004-115630.

The polymer should preferably have a weight average molecular weight (Mw) of 2,000 to 50,000, and more preferably 3,000 to 20,000. A Mw of at least 2,000 eliminates the risk that pattern features are rounded at their top, and resolution and LER are degraded. A Mw of up to 50,000 eliminates the risk that LER is increased. Mw is preferably controlled to or below 20,000 particularly when a pattern with a line width of up to 100 nm is formed. As used herein, Mw is measured by GPC versus polystyrene standards using tetrahydrofuran (THF) solvent.

The polymer preferably has a narrow molecular weight distribution or dispersity (Mw/Mn) of 1.0 to 2.0, more preferably 1.0 to 1.8. A polymer with such a narrow dispersity eliminates any foreign particles left on the pattern or profile degradation of the pattern after development.

The base polymer as component (B) may contain another polymer other than the above-defined polymer. The other polymer may be selected from prior art well-known polymers used in resist materials. The amount of the other polymer is not particularly limited as long as the benefits of the invention are not compromised.

(C) Organic Solvent

The resist composition may further comprise (C) an organic solvent. The organic solvent used herein is not particularly limited as long as the components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, propylene glycol monomethyl ether, cyclohexanone, ethyl lactate, γ-butyrolactone, and mixtures thereof.

An appropriate amount of the organic solvent (C) used is 200 to 10,000 parts, more preferably 400 to 5,000 parts by weight per 100 parts by weight of the base polymer (B).

(D) Fluorinated Polymer

The resist composition may further comprise (D) a fluorinated polymer comprising recurring units having the formula (D1) and recurring units of at least one type selected from recurring units having the formulae (D2), (D3), (D4), and (D5), for the purposes of enhancing contrast, preventing chemical flare of acid upon exposure to high-energy radiation, preventing mixing of acid from an anti-charging film in the step of coating an anti-charging film-forming material on a resist film, and suppressing unexpected unnecessary pattern degradation. Notably, recurring units having formulae (D1), (D2), (D3), (D4), and (D5) are simply referred to as recurring units (D1), (D2), (D3), (D4), and (D5), respectively. Since the fluorinated polymer also has a surface active function, it can prevent insoluble residues from re-depositing onto the substrate during the development step and is thus effective for preventing development defects.

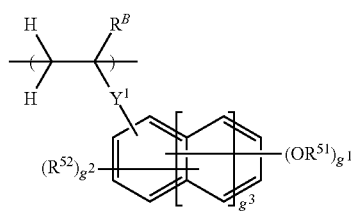

(D1)

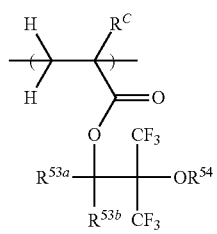

(D2)

-continued

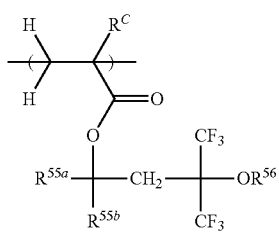
(D3)

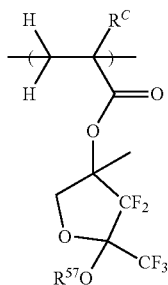
(D4)

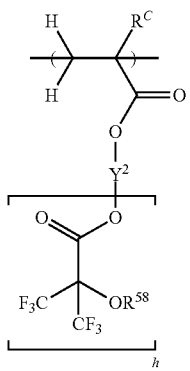
(D5)

Herein $R^B$ is hydrogen or methyl. $R^C$ is each independently hydrogen, fluorine, methyl or trifluoromethyl. $R^{51}$ is hydrogen or a $C_1$-$C_5$ straight or branched monovalent hydrocarbon group in which a heteroatom-containing moiety may intervene in a carbon-carbon bond. $R^{52}$ is a $C_1$-$C_5$ straight or branched monovalent hydrocarbon group in which a heteroatom-containing moiety may intervene in a carbon-carbon bond. $R^{53a}$, $R^{53b}$, $R^{55a}$ and $R^{55b}$ are each independently hydrogen or a $C_1$-$C_{10}$ alkyl group. $R^{54}$, $R^{56}$, $R^{57}$ and $R^{58}$ are each independently hydrogen, a $C_1$-$C_{15}$ monovalent hydrocarbon group, $C_1$-$C_{15}$ monovalent fluorinated hydrocarbon group, or acid labile group, with the proviso that an ether bond or carbonyl moiety may intervene in a carbon-carbon bond in the monovalent hydrocarbon groups or monovalent fluorinated hydrocarbon groups represented by $R^{54}$, $R^{56}$, $R^{57}$ and $R^{58}$. $Y^1$ is a single bond, —C(=O)—O— or —C(=O)—NH—. $Y^2$ is a $C_1$-$C_{20}$ (h+1)-valent hydrocarbon group or $C_1$-$C_{20}$ (h+1)-valent fluorinated hydrocarbon group. The subscript $g^1$ is an integer of 1 to 3, $g^2$ is an integer satisfying $0 \leq g^2 \leq 5+2g^3-g^1$, $g^3$ is 0 or 1, and h is an integer of 1 to 3.

The monovalent hydrocarbon group may be straight, branched or cyclic. Examples include alkyl, alkenyl and alkynyl groups, with the alkyl groups being preferred. Suitable alkyl groups include methyl, ethyl, n-propyl, isopropyl, n-butyl, isobutyl, sec-butyl, and n-pentyl. In these groups, a moiety containing a heteroatom such as oxygen, sulfur or nitrogen may intervene in a carbon-carbon bond.

In formula (D1), —OR$^{51}$ is preferably a hydrophilic group. In this case, R$^{51}$ is preferably hydrogen or a $C_1$-$C_5$ alkyl group in which oxygen (ether bond) intervenes in a carbon-carbon bond.

In formula (D1), Y$^1$ is preferably —C(=O)—O— or —C(=O)—NH—. Also preferably R$^B$ is methyl. The inclusion of carbonyl in Y$^1$ enhances the ability to trap the acid originating from the anti-charging film. A polymer wherein R$^B$ is methyl is a rigid polymer having a high glass transition temperature (Tg) which is effective for suppressing acid diffusion. As a result, the stability with time of a resist film is improved, and neither resolution nor pattern profile is degraded.

Examples of the recurring unit (D1) are given below, but not limited thereto. Herein R$^B$ is as defined above.

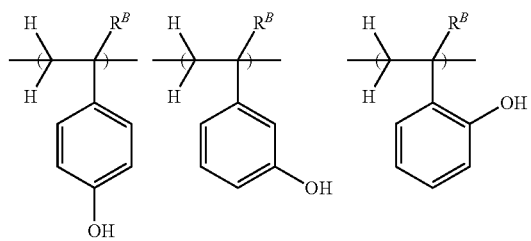

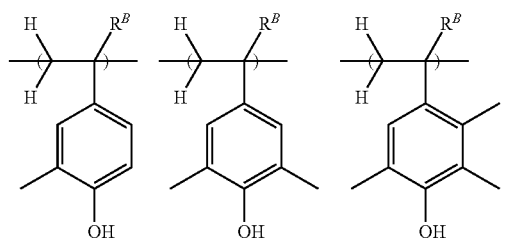

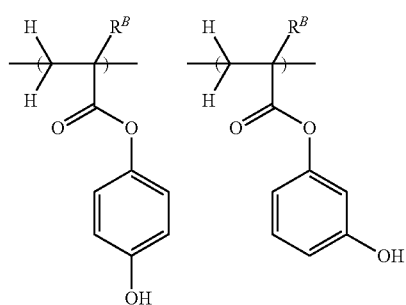

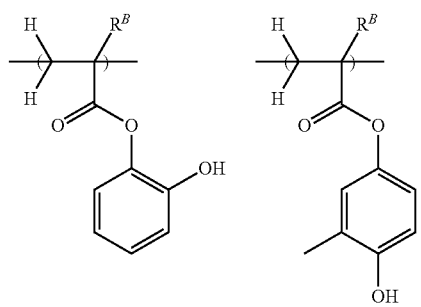

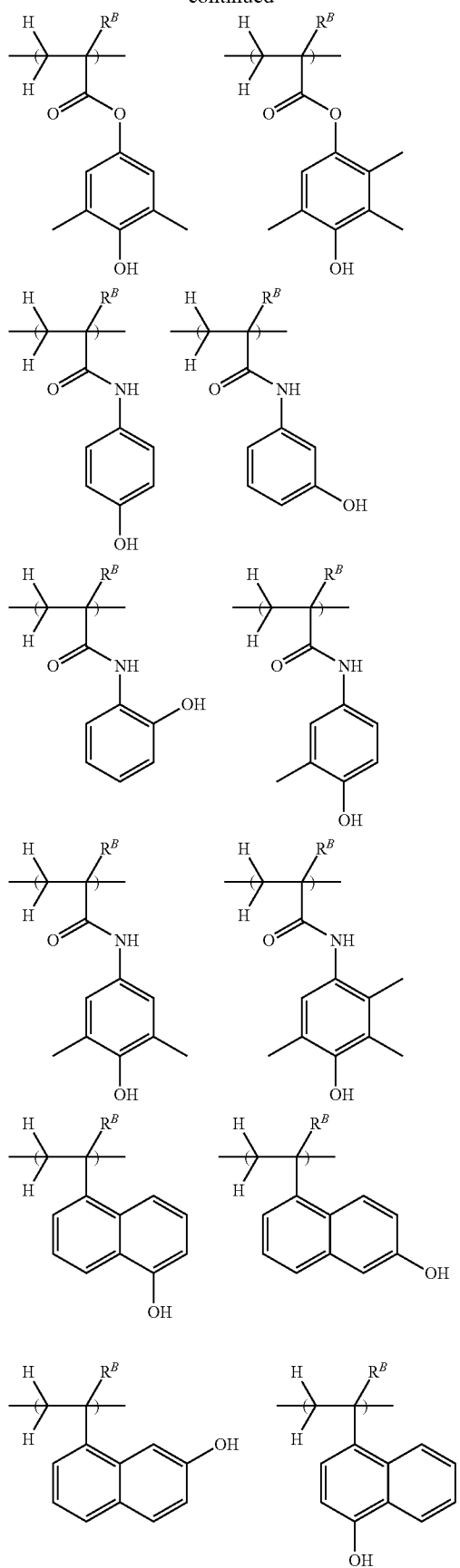
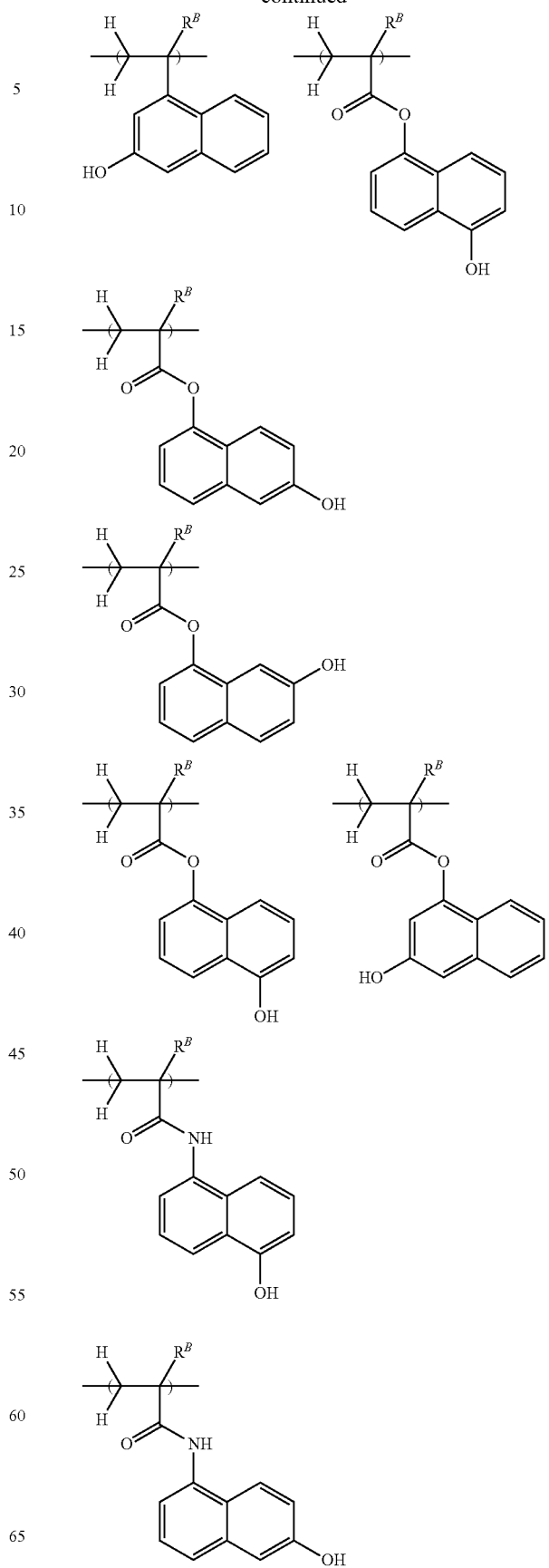

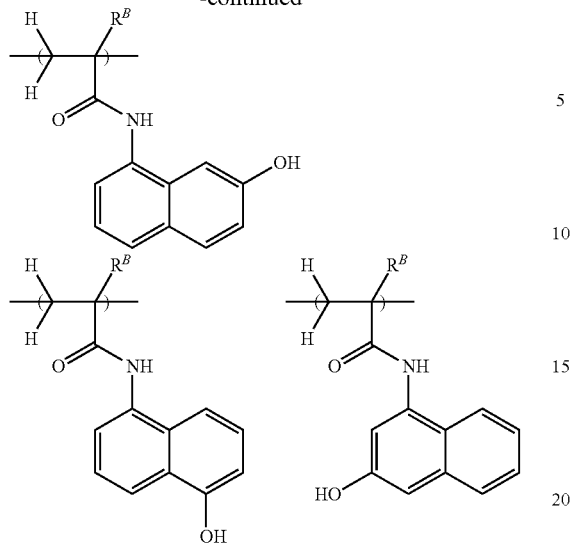

In formulae (D2) and (D3), examples of the alkyl group represented by $R^{53a}$, $R^{53b}$, $R^{55a}$ and $R^{55b}$ include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbornyl. Inter alia, $C_1$-$C_6$ straight, branched or cyclic alkyl groups are preferred.

In formulae (D2) to (D5), examples of the monovalent hydrocarbon group represented by $R^{54}$, $R^{56}$, $R^{57}$ and $R^{58}$ include alkyl, alkenyl and alkynyl groups, with the alkyl groups being preferred. Suitable alkyl groups include n-undecyl, n-dodecyl, tridecyl, tetradecyl and pentadecyl as well as those exemplified above. The monovalent fluorinated hydrocarbon groups correspond to the foregoing monovalent hydrocarbon groups in which some or all carbon-bonded hydrogen atoms are substituted by fluorine.

Examples of the $C_1$-$C_{20}$ (h+1)-valent hydrocarbon or fluorinated hydrocarbon group include the foregoing monovalent hydrocarbon groups and monovalent fluorinated hydrocarbon groups, with a number (h) of hydrogen atoms being eliminated.

Examples of the recurring units (D2) to (D5) are given below, but not limited thereto. Herein $R^C$ is as defined above.

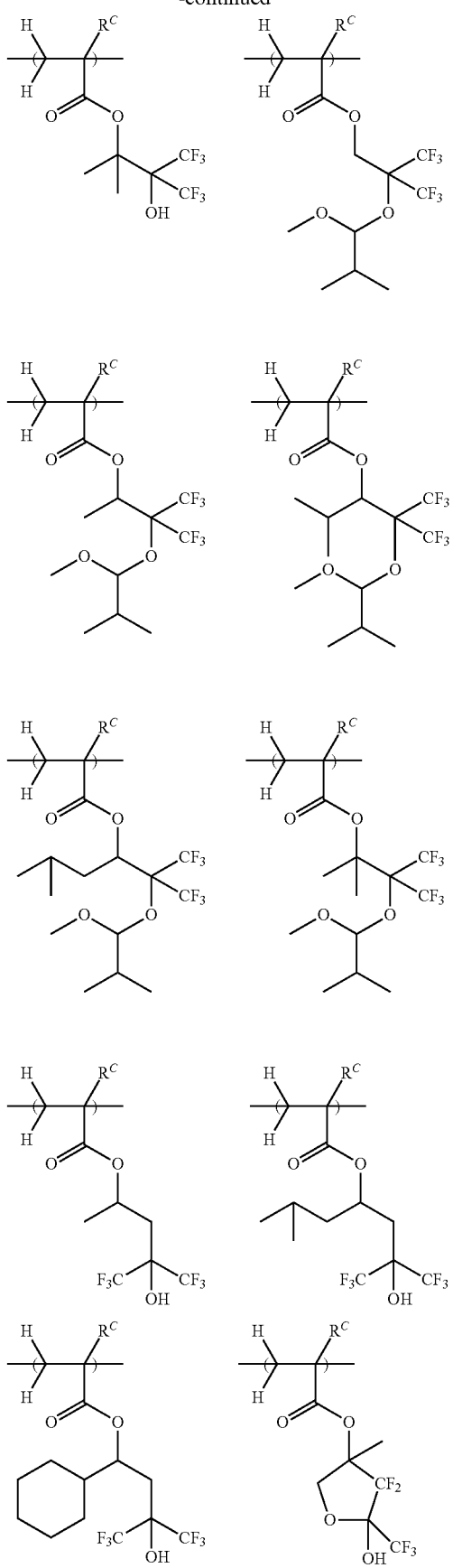

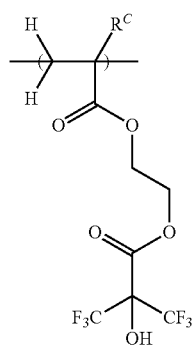 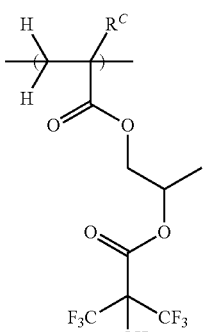 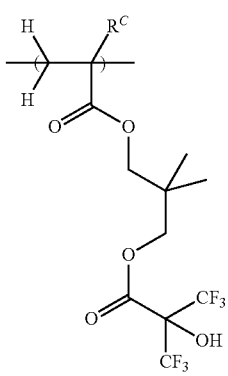 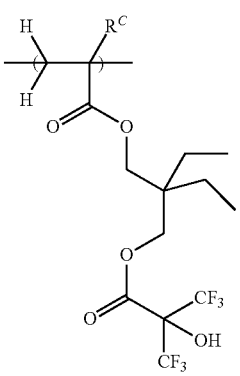
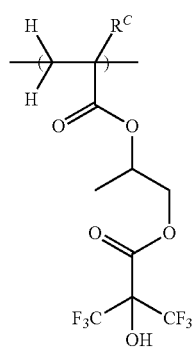 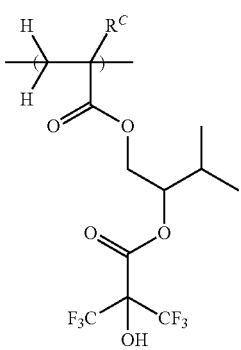 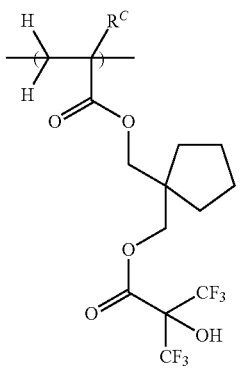
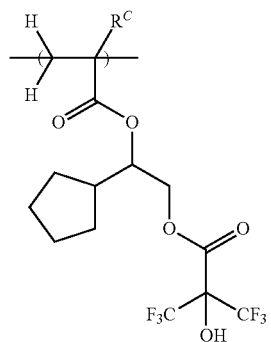 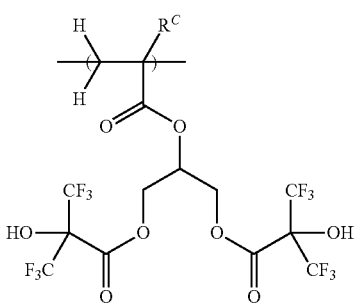
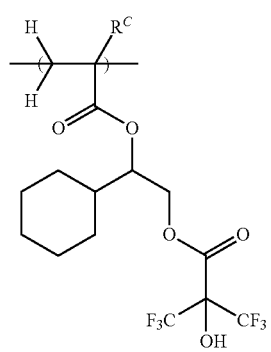 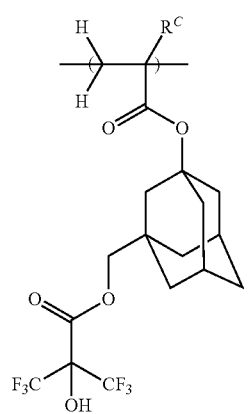 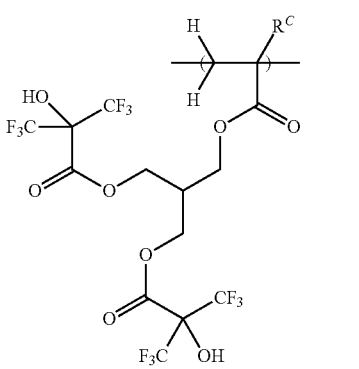

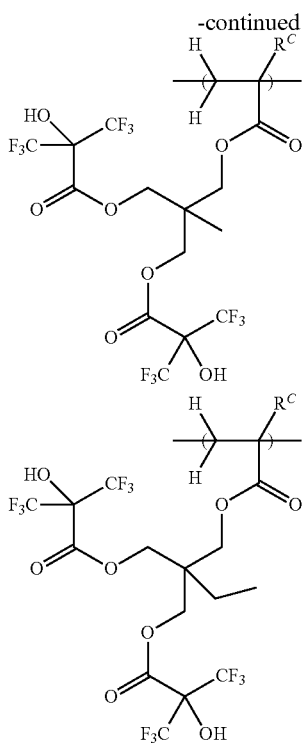

The recurring unit (D1) is preferably incorporated in an amount of 5 to 85 mol %, more preferably 15 to 80 mol % based on the overall recurring units of the fluorinated polymer (D). The recurring units (D2) to (D5), which may be used alone or in admixture, are preferably incorporated in an amount of 15 to 95 mol %, more preferably 20 to 85 mol % based on the overall recurring units of the fluorinated polymer (D).

The fluorinated polymer (D) may comprise additional recurring units as well as the recurring units (D1) to (D5). Suitable additional recurring units include those described in U.S. Pat. No. 9,091,918 (JP-A 2014-177407, paragraphs [0046]-[140078]). When the fluorinated polymer (D) comprises additional recurring units, their content is preferably up to 50 mol % based on the overall recurring units.

The fluorinated polymer (D) may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to JP-A 2004-115630.

The fluorinated polymer (D) should preferably have a weight average molecular weight (Mw) of 2,000 to 50,000, and more preferably 3,000 to 20,000. A fluorinated polymer with a Mw of less than 2,000 helps acid diffusion, degrading resolution and detracting from age stability. A polymer with too high Mw has a reduced solubility in solvent, leading to coating defects. The fluorinated polymer preferably has a dispersity (Mw/Mn) of 1.0 to 2.2, more preferably 1.0 to 1.7.

The fluorinated polymer (D) is preferably used in an amount of 0.01 to 30 parts, more preferably 0.1 to 20 parts by weight per 100 parts by weight of the base polymer (B).

(E) Quencher

The resist composition may further contain (E) a quencher, if desired. The quencher is a compound having a function of trapping the acid generated by the acid generator. The quencher is effective for holding down the rate of diffusion of the acid (generated by the acid generator) in the resist film. Even when a substrate whose outermost surface is made of a chromium-containing material is used as a processable substrate, the quencher is effective for suppressing the influence of the acid (generated in the resist film) on the chromium-containing material.

One preferred example of the quencher is an onium salt of carboxylic acid having the formula (Q-A).

In formula (Q-A), $R^{101}$ is a $C_1$-$C_{40}$ monovalent hydrocarbon group which may contain a heteroatom. The monovalent hydrocarbon group may be straight, branched or cyclic. Examples include $C_1$-$C_{40}$ alkyl groups, $C_2$-$C_{40}$ alkenyl groups, $C_2$-$C_{40}$ alkynyl groups, $C_6$-$C_{40}$ aryl groups, and $C_7$-$C_{40}$ aralkyl groups. In these hydrocarbon groups, some or all hydrogen may be substituted by a hydroxyl, carboxyl, halogen, cyano, amide, nitro, mercapto, sultone, sulfone or sulfonium salt-containing moiety, and some carbon may be replaced by an ether bond, ester bond, carbonyl moiety, carbonate moiety or sulfonic acid ester bond.

In formula (Q-A), $Q^+$ is an onium cation. Suitable onium cations include sulfonium, iodonium and ammonium cations, with the sulfonium cations being preferred. Preferred sulfonium cations are as exemplified above for the sulfonium cation having formula (2).

When the carboxylic onium salt having formula (Q-A) is contained as the quencher, its content is preferably 0.1 to 40 parts by weight, more preferably 0.1 to 20 parts by weight per 100 parts by weight of the base polymer (B).

Another preferred example of the quencher is an onium salt of carboxylic acid having the formula (Q-B) or (Q-C).

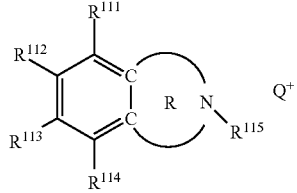

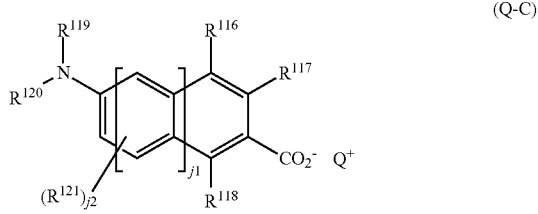

Herein, $Q^+$ is as defined above.

In formula (Q-B), $R^{111}$ to $R^{114}$ are each independently hydrogen, -$L^A$-$CO_2^-$, or a $C_1$-$C_{20}$ monovalent hydrocarbon group which may contain a heteroatom. A pair of $R^{111}$ and $R^{112}$, $R^{112}$ and $R^{113}$, or $R^{113}$ and $R^{114}$ may bond together to form a ring with the carbon atoms to which they are attached. $L^A$ is a single bond or a $C_1$-$C_{20}$ divalent hydrocarbon group which may contain a heteroatom. $R^{115}$ is hydrogen or a $C_1$-$C_{20}$ monovalent hydrocarbon group which may contain a heteroatom.

In formula (Q-B), the ring R is a ring of 2 to 6 carbon atoms including the carbon and nitrogen atoms depicted in the formula, in which some or all of the carbon-bonded hydrogen atoms may be substituted by a $C_1$-$C_{20}$ monovalent hydrocarbon moiety or -$L^A$-$CO_2^-$, or some carbon may be replaced by sulfur, oxygen or nitrogen. The ring may be alicyclic or aromatic and is preferably a 5- or 6-membered ring. Examples include pyridine, pyrrole, pyrrolidine, piperidine, pyrazole, imidazoline, pyridazine, pyrimidine, pyrazine, imidazoline, oxazole, thiazole, morpholine, thiazine, and triazole rings.

The carboxylic onium salt having formula (Q-B) has at least one -$L^A$-$CO_2^-$ group.

In formula (Q-C), $R^{116}$ to $R^{121}$ are each independently hydrogen or a $C_1$-$C_{20}$ monovalent hydrocarbon group which may contain a heteroatom. A pair of $R^{116}$ and $R^{117}$, or $R^{118}$ and $R^{121}$ may bond together to form a ring with the carbon atoms to which they are attached, and a pair of $R^{119}$ and $R^{120}$ may bond together to form a ring with the nitrogen atom to which they are attached. The subscript j1 is 0 or 1, and j2 is 0 or 1 in case of j1=0 and j2 is an integer of 0 to 3 in case of j1=1.

When the carboxylic onium salt having formula (Q-B) or (Q-C) is contained as the quencher, its content is preferably 0.1 to 50 parts by weight, more preferably 0.5 to 30 parts by weight per 100 parts by weight of the base polymer (B).

A further preferred example of the quencher is a sulfonium compound having the formula (Q-D).

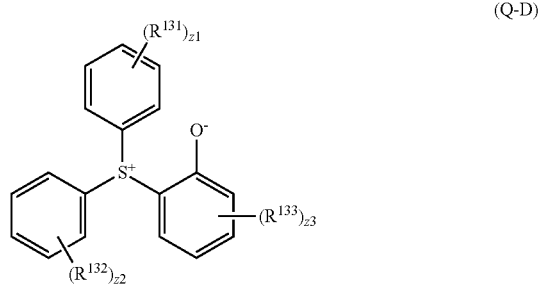

(Q-D)

In formula (Q-D), $R^{131}$, $R^{132}$ and $R^{133}$ are each independently a $C_1$-$C_{20}$ monovalent hydrocarbon group which may contain a heteroatom. In the hydrocarbon group, some hydrogen may be substituted by a moiety containing a heteroatom such as oxygen, sulfur, nitrogen or halogen, or some carbon may be replaced by a moiety containing a heteroatom such as oxygen, sulfur or nitrogen, or the carbon atom (in the hydrocarbon group) bonded to the benzene ring may be replaced by a moiety containing a heteroatom such as oxygen, sulfur or nitrogen, so that the group may contain a hydroxyl moiety, cyano moiety, carbonyl moiety, ether bond, thioether bond, ester bond, sulfonic acid ester bond, carbonate bond, carbamate bond, lactone ring, sultone ring, carboxylic anhydride or haloalkyl moiety.

In formula (Q-D), z1 and z2 are each independently an integer of 0 to 5, and z3 is an integer of 0 to 4. From the standpoints of ease of synthesis and availability of reactants, z1, z2 and z3 each are preferably 0, 1 or 2.

When z1 is 2 to 5, two adjoining $R^{131}$ may bond together to form a ring with the carbon atoms to which they are attached. When z2 is 2 to 5, two adjoining $R^{132}$ may bond together to form a ring with the carbon atoms to which they are attached. When z3 is 2 to 4, two adjoining $R^{133}$ may bond together to form a ring with the carbon atoms to which they are attached.

When the sulfonium compound having formula (Q-D) is contained as the quencher, its content is preferably 0.1 to 40 parts by weight, more preferably 1 to 20 parts by weight per 100 parts by weight of the base polymer (B).

In combination with the above-mentioned onium salt compound, a photo-decomposable onium salt having a nitrogen-containing substituent group may be used as the quencher, if desired. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595, 2012-046501 and JP-A 2013-209360, for example.

When the photo-degradable base is contained as the quencher, its content is preferably 0.1 to 40 parts by weight, more preferably 0.1 to 20 parts by weight per 100 parts by weight of the base polymer (B).

Also, an amine compound may be used as the quencher. Suitable amine compounds include primary, secondary and tertiary amine compounds as described in JP-A 2008-111103, paragraphs [0146]-[0164] (U.S. Pat. No. 7,537,880), especially amine compounds having a hydroxyl group, ether bond, ester bond, lactone ring, cyano group or sulfonic acid ester bond. Also useful are compounds having primary or secondary amine protected with a carbamate group, as described in JP 3790649. When the amine compound is contained as the quencher, its content is preferably 0.001 to 12 parts by weight, more preferably 0.1 to 8 parts by weight per 100 parts by weight of the base polymer (B).

Other Components

Optionally, the resist composition may further comprise a surfactant which is commonly used for facilitating the coating operation. It may be selected from numerous well-known surfactants as described in WO 2006/121096, JP-A 2008-102383, JP-A 2008-304590, JP-A 2004-115630, and JP-A 2005-008766 and in accordance with the teaching thereof. The surfactant may be added in an amount of preferably up to 2 parts, more preferably 0.01 to 1 part by weight per 100 parts by weight of the base polymer (B).

Patterning Process

A further embodiment of the invention is a resist pattern forming process comprising the steps of applying the resist composition onto a substrate to form a resist film thereon, exposing the resist film patternwise to high-energy radiation, and developing the resist film in an alkaline developer to form a resist pattern.

For pattern formation from the resist composition, any well-known lithography processes may be used. In general, the resist composition is applied onto a substrate on which an integrated circuit is to be formed (e.g., Si, SiO, $SiO_2$, SiN, SiON, TiN, WSi, BPSG, SOG or organic antireflective coating) or a substrate on which a mask circuit is to be formed (e.g., Cr, CrO, CrON, $MoSi_2$, Si, SiO or $SiO_2$) by a suitable coating technique, typically spin coating. The coating is prebaked on a hot plate at a temperature of 60 to 150° C. for 1 to 20 minutes, preferably at 80 to 140° C. for 1 to 10 minutes. The resulting resist film is typically 0.03 to 2 μm thick.

Then the resist film is exposed patternwise to high-energy radiation such as UV, deep-UV, EUV, excimer laser light (KrF, ArF), x-ray, γ-ray, synchrotron radiation or EB. On use of UV, deep-UV, EUV, excimer laser or x-ray as the high-energy radiation, the resist film is exposed through a mask having a desired pattern, preferably in a dose of 1 to 300 $mJ/cm^2$, more preferably 10 to 200 $mJ/cm^2$. Alternatively, a pattern may be directly written with EB, preferably in a dose of 1 to 300 μC/cm², more preferably 10 to 200 μC/cm². The chemically amplified resist composition of the invention is advantageous particularly in the EUV or EB lithography. Light exposure may be done by a conventional lithography process or in some cases, by an immersion lithography process of providing liquid immersion, typically water, between the mask and the resist film. In the case of immersion lithography, a protective film which is insoluble in water may be used.

The resist film is further baked (PEB) on a hot plate at 60 to 150° C. for 1 to 20 minutes, preferably at 80 to 140° C. for 1 to 10 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray techniques. In this way, a desired positive resist pattern is formed on the substrate.

The resist composition of the invention is advantageously used under the situation that requires high etching resistance, and a minimal change of pattern line width and minimal LER even when the time duration from exposure to PEB is prolonged. The resist composition is also advantageous for pattern formation on a substrate having a surface layer of material to which the resist pattern is less adherent with a likelihood of pattern stripping or pattern collapse, specifically a substrate having sputter deposited thereon a layer of metallic chromium or a chromium compound containing one or more light elements such as oxygen, nitrogen and carbon. The resist composition is advantageous particularly in pattern formation using a photomask blank as the substrate.

EXAMPLES

Examples and Comparative Examples are given below by way of illustration and not by way of limitation. All parts are by weight (pbw); THF stands for tetrahydrofuran; Mw is a weight average molecular weight as measured versus polystyrene standards by GPC using THF solvent. The copolymer compositional ratio is a molar ratio.

[1] Synthesis of Sulfonium Salts

Example 1-1

Synthesis of triphenylsulfonium 4-(2,4,6-trinorbornylbenzenesulfonyloxy)benzenesulfonate (PAG-1)

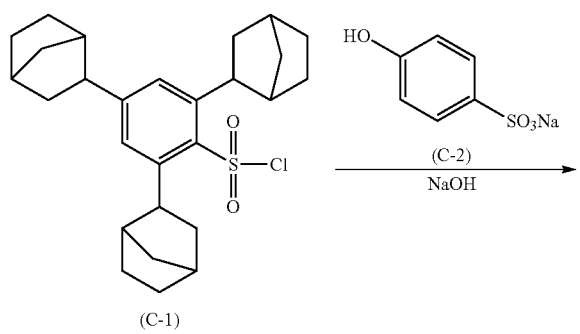

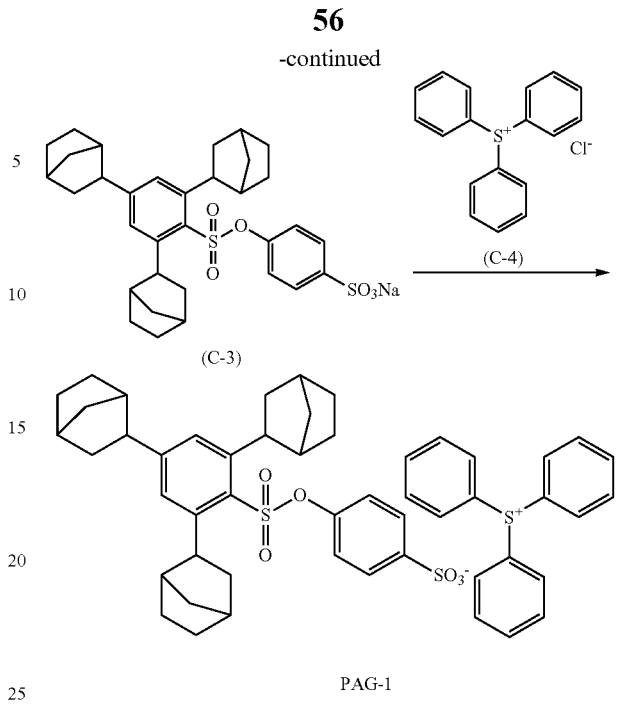

PAG-1

In a mixture of 20 g of THF and 15 g of H₂O was suspended 4.32 g of sodium 4-hydroxybenzenesulfonate (C-2). Under ice cooling, 3.20 g of 25 wt % NaOH was added dropwise to the suspension, which was stirred for 1 hour. A solution of 4.59 g of 2,4,6-trinorbornylbenzenesulfonyl chloride (C-1) in 25 g of THF was added dropwise to the solution, which was stirred for 3 hours at room temperature until sodium 4-(2,4,6-trinorbornylbenzenesulfonyloxy)benzenesulfonate (C-3) was obtained. Next, 50 g of a 5 wt % aqueous solution of triphenylsulfonium chloride (C-4) and 50 g of methylene chloride were added to the reaction solution. After 30 minutes of stirring, the organic layer was taken out, washed with water, and concentrated under reduced pressure. Methyl isobutyl ketone, 10 mL, was added to the concentrate, which was concentrated again. The precipitated solid was washed with diisopropyl ether and dried in vacuum. The target compound was obtained, i.e., 4.04 g of triphenylsulfonium 4-(2,4,6-trinorbornylbenzenesulfonyloxy)benzenesulfonate, designated PAG-1, as white crystal (yield 47%).

Example 1-2

Synthesis of triphenylsulfonium 2-isopropyl-5-methyl-4-(2,4,6-trinorbornylbenzenesulfonyloxy) benzenesulfonate (PAG-2)

Synthesis was carried out as in Example 1-1 aside from using sodium 2-isopropyl-5-methyl-4-hydroxybenzenesulfonate instead of sodium 4-hydroxybenzenesulfonate (C-2). There was obtained 3.94 g of PAG-2 (yield 43%).

Example 1-3

Synthesis of 10-phenylphenoxathiinium 2-isopropyl-5-methyl-4-(2,4,6-trinorbornylbenzenesulfonyloxy)benzenesulfonate (PAG-3)

Synthesis was carried out as in Example 1-1 aside from using an aqueous solution of 10-phenylphenoxathiinium chloride instead of the aqueous solution of triphenylsulfonium chloride (C-4). There was obtained 4.72 g of PAG-3 (yield 51%).

Example 1-4

Synthesis of 10-phenylphenoxathiinium 2-isopropyl-5-methyl-4-(2,4,6-trioxa-norbornylbenzenesulfonyloxy)benzenesulfonate (PAG-4)

Synthesis was carried out as in Example 1-1 aside from using 2,4,6-trioxanorbornyl-benzenesulfonyl chloride instead of 2,4,6-trinorbornylbenzenesulfonyl chloride (C-1), sodium 2-isopropyl-5-methyl-4-hydroxybenzenesulfonate instead of sodium 4-hydroxybenzenesulfonate (C-2), and an aqueous solution of 10-phenylphenoxathiinium chloride instead of the aqueous solution of triphenylsulfonium chloride (C-4). There was obtained 4.40 g of PAG-4 (yield 47%).

Example 1-5

Synthesis of 10-phenylphenoxathiinium 2,6-diisopropyl-4-(2,4,6-trinorbornylbenzenesulfonyloxy)benzenesulfonate (PAG-5)

Synthesis was carried out as in Example 1-1 aside from using sodium 2,6-diisopropyl-4-hydroxybenzenesulfonate instead of sodium 4-hydroxybenzenesulfonate (C-2), and an aqueous solution of 10-phenylphenoxathiinium chloride instead of the aqueous solution of triphenylsulfonium chloride (C-4). There was obtained 5.27 g of PAG-5 (yield 55%).

Example 1-6

Synthesis of 10-phenylphenoxathiinium 4-{2,4,6-tri(7,7-dimethylnorbornyl)benzenesulfonyloxy}benzenesulfonate (PAG-6)

Synthesis was carried out as in Example 1-1 aside from using 2,4,6-tri(7,7-dimethyl-norbornyl)benzenesulfonyl chloride instead of 2,4,6-trinorbornylbenzenesulfonyl chloride (C-1), and an aqueous solution of 10-phenylphenoxathiinium chloride instead of the aqueous solution of triphenylsulfonium chloride (C-4). There was obtained 4.83 g of PAG-6 (yield 51%).

[2] Synthesis of Base Polymers

Synthesis Example 1-1

Synthesis of Polymer A1

A 3-L flask was charged with 407.5 g of acetoxystyrene, 42.5 g of acenaphthylene, and 1,275 g of toluene as solvent. The reactor was cooled at −70° C. in a nitrogen atmosphere, after which vacuum pumping and nitrogen blow were repeated three times. The reactor was warmed up to room temperature, whereupon 34.7 g of 2,2'-azobis(2,4-dimethylvalero-nitrile) (V-65 by Wako Pure Chemical Industries, Ltd.) was added. The reactor was heated at 55° C., whereupon reaction ran for 40 hours. After the completion of reaction, with stirring, a mixture of 970 g of methanol and 180 g of water was added dropwise to the reaction solution. After 30 minutes of standing, the lower layer (polymer layer) was concentrated under reduced pressure. The polymer layer concentrate was dissolved again in 0.45 L of methanol and 0.54 L of THF, to which 160 g of triethylamine and 30 g of water were added. The reaction mixture was heated at 60° C. for 40 hours for deprotection reaction. The reaction solution was concentrated under reduced pressure. To the concentrate, 548 g of methanol and 112 g of acetone were added for dissolution. With stirring, 990 g of hexane was added dropwise to the solution. After 30 minutes of standing, the lower layer (polymer layer) was taken out and 300 g of THF was added thereto. With stirring, 1,030 g of hexane was added dropwise thereto. After 30 minutes of standing, the lower layer (polymer layer) was concentrated under reduced pressure. The concentrated polymer solution was neutralized with 82 g of acetic acid. The reaction solution was concentrated, dissolved in 0.3 L of acetone, and poured into 10 L of water for precipitation. The precipitate was filtered and dried, yielding 280 g of a white polymer. The polymer was analyzed by $^1$H-NMR and GPC, with the results shown below.

Copolymer compositional ratio
hydroxystyrene:acenaphthylene=89.3:10.7
Mw=5,000
Mw/Mn=1.63

Under acidic conditions, 100 g of the polymer was reacted with 47.5 g of (2-methyl-1-propenyl)-8-(tricyclo[5.2.1.0$^{2,6}$] decanyl ether. This was followed by neutralization, separatory operation, and crystallization, obtaining 130 g of Polymer A1, as shown in Table 1.

Synthesis Examples 1-2 to 1-9

Synthesis of Polymers A2, A3, A5 to A10

Polymers A2, A3, A5 to A10 as shown in Table 1 were synthesized by the same procedure as in Synthesis Example 1-1 except that the type and amount of monomers were changed.

Synthesis Example 1-10

Synthesis of Polymer A4

In nitrogen atmosphere, 65.0 g of 4-acetoxystyrene, 8.9 g of acenaphthylene, 25.3 g of methylcyclohexyloxystyrene, 9.0 g of dimethyl 2,2'-azobis(2-methylpropionate) (V-601 by Wako Pure Chemical Industries, Ltd.), and 180 g of methyl ethyl ketone (MEK) were fed into a dropping cylinder to form a monomer solution. A flask in nitrogen atmosphere was charged with 120 g of MEK, which was heated at 80° C. with stirring. With stirring, the monomer solution was added dropwise to the flask over 4 hours. After the completion of dropwise addition, the polymerization solution was continuously stirred for 18 hours while maintaining its temperature at 80° C. The polymerization solution was cooled to room temperature, whereupon it was added dropwise to 1.5 kg of hexane. The precipitated copolymer was collected by filtration and washed twice with 300 g of hexane. The copolymer was dissolved in a mixture of 180 g of THF and 60 g of methanol, to which 20.6 g of ethanolamine was added. The solution was stirred for 3 hours under reflux, after which it was concentrated under reduced pressure. The concentrate was dissolved in ethyl acetate. This was followed by neutralization, separatory operation, and crystallization, obtaining 82 g of Polymer A4, as shown in Table 1.

Synthesis Examples 1-11 to 1-14

Synthesis of Polymers A11 to A14

Polymers A11 to A14 as shown in Table 1 were synthesized by the same procedure as in Synthesis Example 1-10 except that the type and amount of monomers were changed.

Synthesis Example 1-15

Synthesis of Polymer A15

In nitrogen atmosphere, 24.2 g of 4-hydroxystyrene, 53.0 g of a monomer providing unit (b-6), 44.2 g of a monomer providing unit (c-6), 89.0 g of a monomer providing unit (d-1), 17.0 g of dimethyl 2,2'-azobis(2-methylpropionate) (V-601 by Wako Pure Chemical Industries, Ltd.), and 96 g of γ-butyrolactone were fed into a dropping cylinder to form a monomer solution. A flask in nitrogen atmosphere was charged with 156 g of γ-butyrolactone, which was heated at 80° C. with stirring. With stirring, the monomer solution was added dropwise to the flask over 4 hours. After the completion of dropwise addition, the polymerization solution was continuously stirred for 18 hours while maintaining its temperature at 80° C. The polymerization solution was cooled to room temperature, whereupon it was added dropwise to 6 kg of diisopropyl ether. The precipitated copolymer was collected by filtration, washed twice with 1.2 kg of diisopropyl ether, and vacuum dried, obtaining Polymer A15.

Synthesis Examples 1-16 to 1-21

Synthesis of Polymers A16 to A21

Polymers A16 to A21 as shown in Table 1 were synthesized by the same procedure as in Synthesis Example 1-15 except that the type and amount of monomers were changed.

Table 1 shows the type and proportion (in molar ratio) of recurring units incorporated in these polymers. Tables 2 to 5 show the structure of recurring units.

TABLE 2

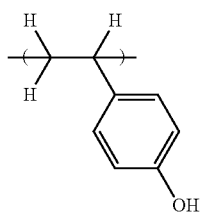
a-1

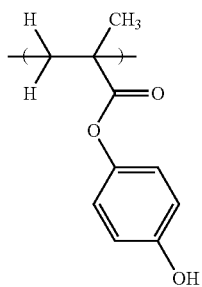
a-2

TABLE 3

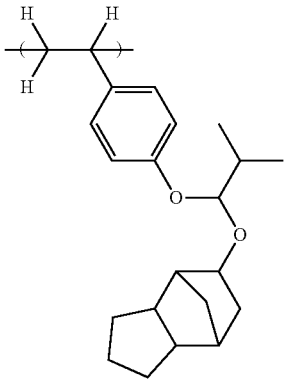 [SMILES: CCC(C)c1ccc(OC(OC2CC3CC2C2CCCC32)C(C)C)cc1]
b-1

TABLE 1

|  | Unit 1 | Proportion (mol %) | Unit 2 | Proportion (mol %) | Unit 3 | Proportion (mol %) | Unit 4 | Proportion (mol %) | Mw | Mw/Mn |
|---|---|---|---|---|---|---|---|---|---|---|
| Polymer A1 | a-1 | 76.0 | b-1 | 12.0 | c-1 | 12.0 | — | — | 5,500 | 1.63 |
| Polymer A2 | a-1 | 76.0 | b-1 | 13.0 | c-2 | 11.0 | — | — | 5,800 | 1.71 |
| Polymer A3 | a-1 | 78.0 | b-2 | 11.0 | c-1 | 11.0 | — | — | 5,500 | 1.65 |
| Polymer A4 | a-1 | 69.0 | b-3 | 21.0 | c-1 | 10.0 | — | — | 4,000 | 1.58 |
| Polymer A5 | a-1 | 73.0 | b-2 | 15.0 | c-3 | 12.0 | — | — | 5,700 | 1.65 |
| Polymer A6 | a-1 | 73.0 | b-2 | 14.0 | c-4 | 13.0 | — | — | 5,400 | 1.70 |
| Polymer A7 | a-1 | 72.0 | b-1 | 16.0 | c-3 | 12.0 | — | — | 5,800 | 1.60 |
| Polymer A8 | a-1 | 72.0 | b-1 | 16.0 | c-4 | 12.0 | — | — | 5,900 | 1.63 |
| Polymer A9 | a-1 | 73.0 | b-2 | 15.0 | c-5 | 12.0 | — | — | 5,700 | 1.80 |
| Polymer A10 | a-1 | 72.0 | b-1 | 16.0 | c-5 | 12.0 | — | — | 5,700 | 1.72 |
| Polymer A11 | a-1 | 67.0 | b-4 | 23.0 | c-1 | 10.0 | — | — | 4,100 | 1.66 |
| Polymer A12 | a-1 | 64.0 | b-4 | 24.0 | c-5 | 12.0 | — | — | 5,400 | 1.65 |
| Polymer A13 | a-1 | 68.0 | b-5 | 20.0 | c-1 | 12.0 | — | — | 4,200 | 1.70 |
| Polymer A14 | a-1 | 68.0 | b-5 | 21.0 | c-5 | 11.0 | — | — | 4,000 | 1.80 |
| Polymer A15 | a-2 | 20.0 | b-6 | 30.0 | c-6 | 30.0 | d-1 | 20.0 | 14,500 | 1.51 |
| Polymer A16 | a-1 | 55.0 | b-4 | 25.0 | c-1 | 10.0 | d-2 | 10.0 | 7,200 | 1.57 |
| Polymer A17 | a-1 | 58.0 | b-5 | 20.0 | c-1 | 9.0 | d-2 | 13.0 | 7,300 | 1.62 |
| Polymer A18 | a-1 | 55.0 | b-5 | 20.0 | c-5 | 12.0 | d-2 | 13.0 | 7,100 | 1.63 |
| Polymer A19 | a-2 | 46.0 | b-7 | 19.0 | c-6 | 35.0 | — | — | 5,500 | 1.56 |
| Polymer A20 | a-2 | 50.0 | b-8 | 15.0 | c-6 | 35.0 | — | — | 5,300 | 1.70 |
| Polymer A21 | a-2 | 67.0 | b-9 | 23.0 | c-6 | 10.0 | — | — | 6,100 | 1.60 |

TABLE 3-continued
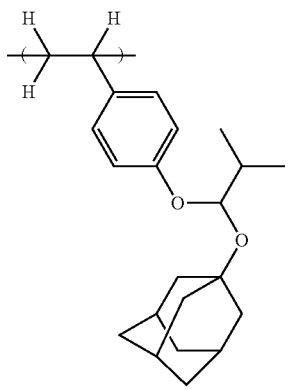 [SMILES: CCC(C)c1ccc(OC(OC23CC4CC(CC(C4)C2)C3)C(C)C)cc1] b-2
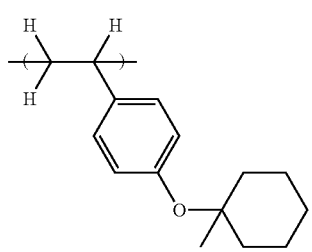 [SMILES: CCC(C)c1ccc(OC2(C)CCCCC2)cc1] b-3
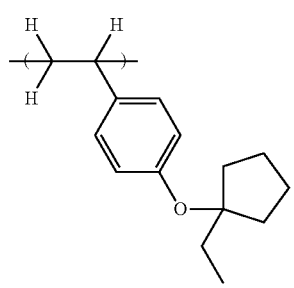 [SMILES: CCC(C)c1ccc(OC2(CC)CCCC2)cc1] b-4
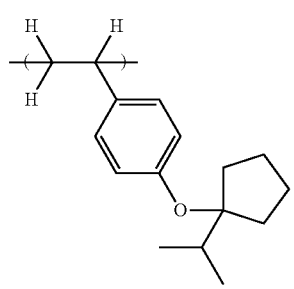 [SMILES: CCC(C)c1ccc(OC2(C(C)C)CCCC2)cc1] b-5
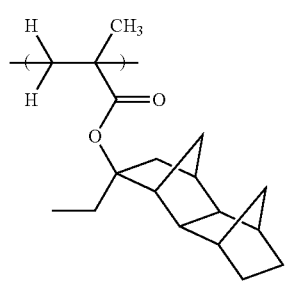 [SMILES: CCC(C)(C)C(=O)OC1(CC)CC2CC1C1C3CCC(C3)C21] b-6
TABLE 3-continued
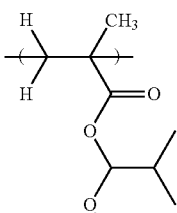 b-7
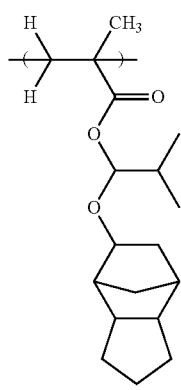 [SMILES: CCC(C)(C)C(=O)OC(OC1CC2CC1C1CCCC21)C(C)C] b-8
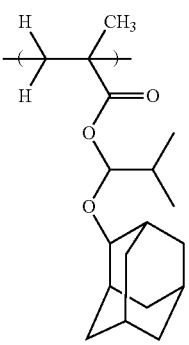 [SMILES: CCC(C)(C)C(=O)OC(OC1C2CC3CC(C2)CC1C3)C(C)C] b-9
TABLE 4
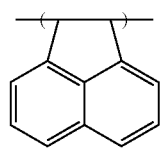 c-1
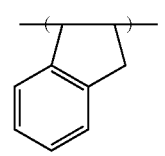 c-2
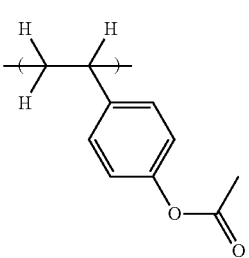 c-3

TABLE 4-continued

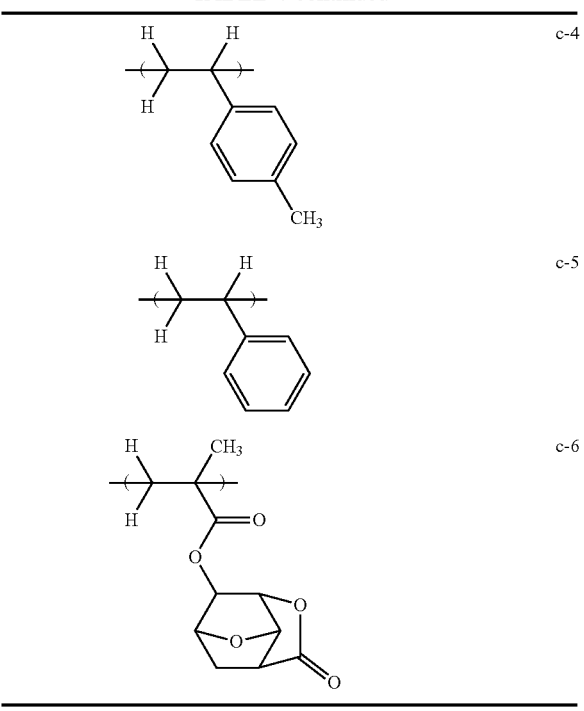

TABLE 5

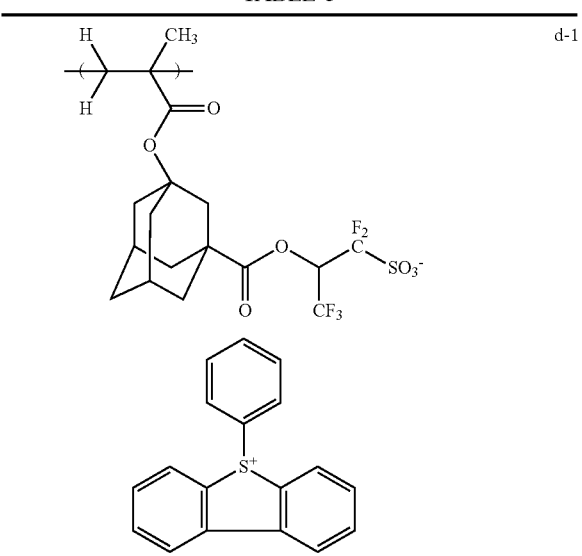

TABLE 5-continued

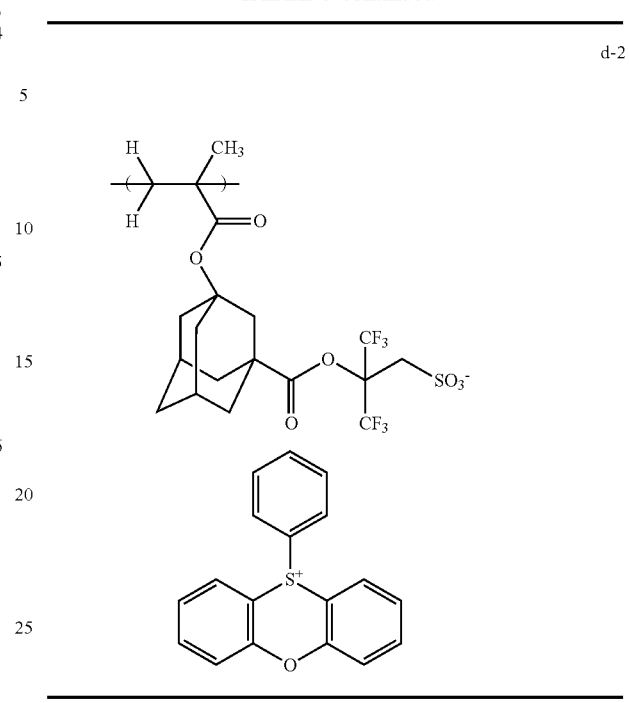

[3] Preparation of Positive Resist Compositions

Examples 2-1 to 2-37 and Comparative Examples 1-1 to 1-6

A positive resist composition in solution form was prepared by dissolving a base polymer (Polymers A1 to A21), an acid generator (PAG-1 to PAG-6, c-PAG-1 to c-PAG-5, PAG-A, PAG-B), a quencher (Q-1 to Q-3), and a fluorinated polymer (Polymers D1 to D3) in an organic solvent in accordance with the recipe shown in Tables 6 to 8, and filtering through a UPE filter with a pore size of 0.02 μm.

In Tables 6 to 8, the organic solvents are PGMEA (propylene glycol monomethyl ether acetate), EL (ethyl lactate), PGME (propylene glycol monomethyl ether), and CyH (cyclohexanone). The composition contained 0.075 part by weight of surfactant PF-636 (Omnova Solutions Inc.) per 100 parts by weight of solids.

TABLE 6

|  |  | Resist composition | Polymer 1 (pbw) | Polymer 2 (pbw) | Acid generator (pbw) | Quencher (pbw) | Fluorinated polymer (pbw) | Solvent 1 (pbw) | Solvent 2 (pbw) | Solvent 3 (pbw) |
|---|---|---|---|---|---|---|---|---|---|---|
| Example | 2-1 | R-1 | Polymer A1 (80) | — | PAG-2 (9) | Q-1 (4.0) | — | PGMEA (1,160) | EL (2,706) | — |
|  | 2-2 | R-2 | Polymer A1 (80) | — | PAG-2 (9) | Q-1 (4.0) | Polymer D1 (3) | PGMEA (1,160) | EL (2,706) | — |
|  | 2-3 | R-3 | Polymer A1 (80) | — | PAG-2 (7) PAG-A (2) | Q-1 (4.0) | — | PGMEA (1,160) | EL (2,706) | — |

TABLE 6-continued

| | Resist composition | Polymer 1 (pbw) | Polymer 2 (pbw) | Acid generator (pbw) | Quencher (pbw) | Fluorinated polymer (pbw) | Solvent 1 (pbw) | Solvent 2 (pbw) | Solvent 3 (pbw) |
|---|---|---|---|---|---|---|---|---|---|
| 2-4 | R-4 | Polymer A1 (80) | — | PAG-2 (7) PAG-B (2) | Q-1 (4.0) | — | PGMEA (1,160) | EL (2,706) | — |
| 2-5 | R-5 | Polymer A1 (80) | — | PAG-2 (12) | Q-1 (5.0) | — | PGMEA (1,160) | EL (2,706) | — |
| 2-6 | R-6 | Polymer A1 (80) | — | PAG-2 (18) | Q-1 (6.0) | — | PGMEA (1,160) | EL (2,706) | — |
| 2-7 | R-7 | Polymer A1 (80) | — | PAG-2 (9) | Q-2 (3.0) | — | PGMEA (1,160) | EL (2,706) | — |
| 2-8 | R-8 | Polymer A1 (80) | — | PAG-2 (9) | Q-3 (2.2) | — | PGMEA (1,160) | EL (2,706) | — |
| 2-9 | R-9 | Polymer A1 (80) | — | PAG-1 (9) | Q-1 (4.0) | — | PGMEA (1,160) | EL (2,706) | — |
| 2-10 | R-10 | Polymer A1 (80) | — | PAG-3 (9) | Q-1 (4.0) | — | PGMEA (1,160) | EL (2,706) | — |
| 2-11 | R-11 | Polymer A1 (80) | — | PAG-4 (9) | Q-1 (4.0) | — | PGMEA (1,160) | EL (2,706) | — |
| 2-12 | R-12 | Polymer A1 (80) | — | PAG-5 (9) | Q-1 (4.0) | — | PGMEA (1,160) | EL (2,706) | — |
| 2-13 | R-13 | Polymer A1 (80) | — | PAG-6 (9) | Q-1 (4.0) | — | PGMEA (1,160) | EL (2,706) | — |
| 2-14 | R-14 | Polymer A2 (80) | — | PAG-2 (9) | Q-1 (4.0) | — | PGMEA (1,160) | EL (2,706) | — |
| 2-15 | R-15 | Polymer A3 (80) | — | PAG-2 (9) | Q-1 (4.0) | — | PGMEA (1,160) | EL (2,706) | — |
| 2-16 | R-16 | Polymer A4 (80) | — | PAG-2 (9) | Q-1 (4.0) | — | PGMEA (1,160) | EL (2,706) | — |
| 2-17 | R-17 | Polymer A5 (80) | — | PAG-2 (9) | Q-1 (4.0) | — | PGMEA (1,160) | EL (2,706) | — |
| 2-18 | R-18 | Polymer A6 (80) | — | PAG-2 (9) | Q-1 (4.0) | — | PGMEA (1,160) | EL (2,706) | — |
| 2-19 | R-19 | Polymer A7 (80) | — | PAG-2 (9) | Q-1 (4.0) | — | PGMEA (1,160) | EL (2,706) | — |
| 2-20 | R-20 | Polymer A8 (80) | — | PAG-2 (9) | Q-1 (4.0) | — | PGMEA (1,160) | EL (2,706) | — |

TABLE 7

| | | Resist composition | Polymer 1 (pbw) | Polymer 2 (pbw) | Acid generator (pbw) | Quencher (pbw) | Fluorinated polymer (pbw) | Solvent 1 (pbw) | Solvent 2 (pbw) | Solvent 3 (pbw) |
|---|---|---|---|---|---|---|---|---|---|---|
| Example | 2-21 | R-21 | Polymer A9 (80) | — | PAG-2 (9) | Q-1 (4.0) | — | PGMEA (1,160) | EL (2,706) | — |
| | 2-22 | R-22 | Polymer A10 (80) | — | PAG-2 (9) | Q-1 (4.0) | — | PGMEA (1,160) | EL (2,706) | — |
| | 2-23 | R-23 | Polymer A10 (80) | — | PAG-3 (9) | Q-3 (2.2) | Polymer D1 (3) | PGMEA (1,160) | EL (2,706) | — |
| | 2-24 | R-24 | Polymer A10 (80) | — | PAG-3 (9) | Q-3 (2.2) | Polymer D2 (3) | PGMEA (1,160) | EL (2,706) | — |
| | 2-25 | R-25 | Polymer A10 (80) | — | PAG-3 (9) | Q-3 (2.2) | Polymer D3 (3) | PGMEA (1,160) | EL (2,706) | — |
| | 2-26 | R-26 | Polymer A11 (80) | — | PAG-2 (9) | Q-1 (4.0) | — | PGMEA (1,160) | EL (2,706) | — |
| | 2-27 | R-27 | Polymer A12 (80) | — | PAG-2 (9) | Q-1 (4.0) | — | PGMEA (1,160) | EL (2,706) | — |
| | 2-28 | R-28 | Polymer A13 (80) | — | PAG-2 (9) | Q-1 (4.0) | — | PGMEA (1,160) | EL (2,706) | — |
| | 2-29 | R-29 | Polymer A14 (80) | — | PAG-2 (9) | Q-1 (4.0) | — | PGMEA (1,160) | EL (2,706) | — |
| | 2-30 | R-30 | Polymer A15 (40) | Polymer A1 (40) | PAG-3 (5) | Q-3 (2.2) | — | PGMEA (386) | EL (1,932) | PGME (1,546) |
| | 2-31 | R-31 | Polymer A16 (80) | Polymer A11 (40) | PAG-3 (5) | Q-3 (2.0) | — | PGMEA (386) | EL (1,932) | PGME (1,546) |
| | 2-32 | R-32 | Polymer A17 (80) | Polymer A13 (40) | PAG-3 (5) | Q-3 (2.0) | — | PGMEA (386) | EL (1,932) | PGME (1,546) |
| | 2-33 | R-33 | Polymer A17 (80) | Polymer A13 (40) | PAG-3 (5) | Q-3 (2.0) | Polymer D1 (3) | PGMEA (386) | EL (1,932) | PGME (1,546) |
| | 2-34 | R-34 | Polymer A18 (80) | Polymer A14 (40) | PAG-3 (5) | Q-3 (2.0) | — | PGMEA (386) | EL (1,932) | PGME (1,546) |
| | 2-35 | R-35 | Polymer A19 (80) | — | PAG-2 (9) | Q-1 (4.0) | — | PGMEA (1,104) | CyH (2,208) | PGME (552) |

TABLE 7-continued

| Resist composition | Polymer 1 (pbw) | Polymer 2 (pbw) | Acid generator (pbw) | Quencher (pbw) | Fluorinated polymer (pbw) | Solvent 1 (pbw) | Solvent 2 (pbw) | Solvent 3 (pbw) |
|---|---|---|---|---|---|---|---|---|
| 2-36 R-36 | Polymer A20 (80) | — | PAG-2 (9) | Q-1 (4.0) | — | PGMEA (1,104) | CyH (2,208) | PGME (552) |
| 2-37 R-37 | Polymer A21 (80) | — | PAG-2 (9) | Q-1 (4.0) | — | PGMEA (1,104) | CyH (2,208) | PGME (552) |

TABLE 8

| | Resist composition | Polymer 1 (pbw) | Polymer 2 (pbw) | Acid generator (pbw) | Quencher (pbw) | Fluorinated polymer (pbw) | Solvent 1 (pbw) | Solvent 2 (pbw) | Solvent 3 (pbw) |
|---|---|---|---|---|---|---|---|---|---|
| Comparative Example | 1-1 CR-1 | Polymer A1 (80) | — | c-PAG-1 (9) | Q-1 (4.0) | — | PGMEA (1,160) | EL (2,706) | — |
| | 1-2 CR-2 | Polymer A1 (80) | — | c-PAG-2 (9) | Q-1 (4.0) | — | PGMEA (1,160) | EL (2,706) | — |
| | 1-3 CR-3 | Polymer A1 (80) | — | c-PAG-3 (9) | Q-1 (4.0) | — | PGMEA (1,160) | EL (2,706) | — |
| | 1-4 CR-4 | Polymer A1 (80) | — | c-PAG-4 (9) | Q-1 (4.0) | — | PGMEA (1,160) | EL (2,706) | — |
| | 1-5 CR-5 | Polymer A1 (80) | — | c-PAG-5 (9) | Q-1 (4.0) | — | PGMEA (1,160) | EL (2,706) | — |
| | 1-6 CR-6 | Polymer A19 (80) | — | c-PAG-1 (9) | Q-1 (4.0) | — | PGMEA (1,160) | EL (2,208) | PGME (552) |

The acid generators (PAG-1 to PAG-6, c-PAG-1 to c-PAG-5, PAG-A, PAG-B), quenchers (Q-1 to Q-3), and fluorinated polymers (Polymers D1 to D3) in Tables 6 to 8 are identified below.

-continued

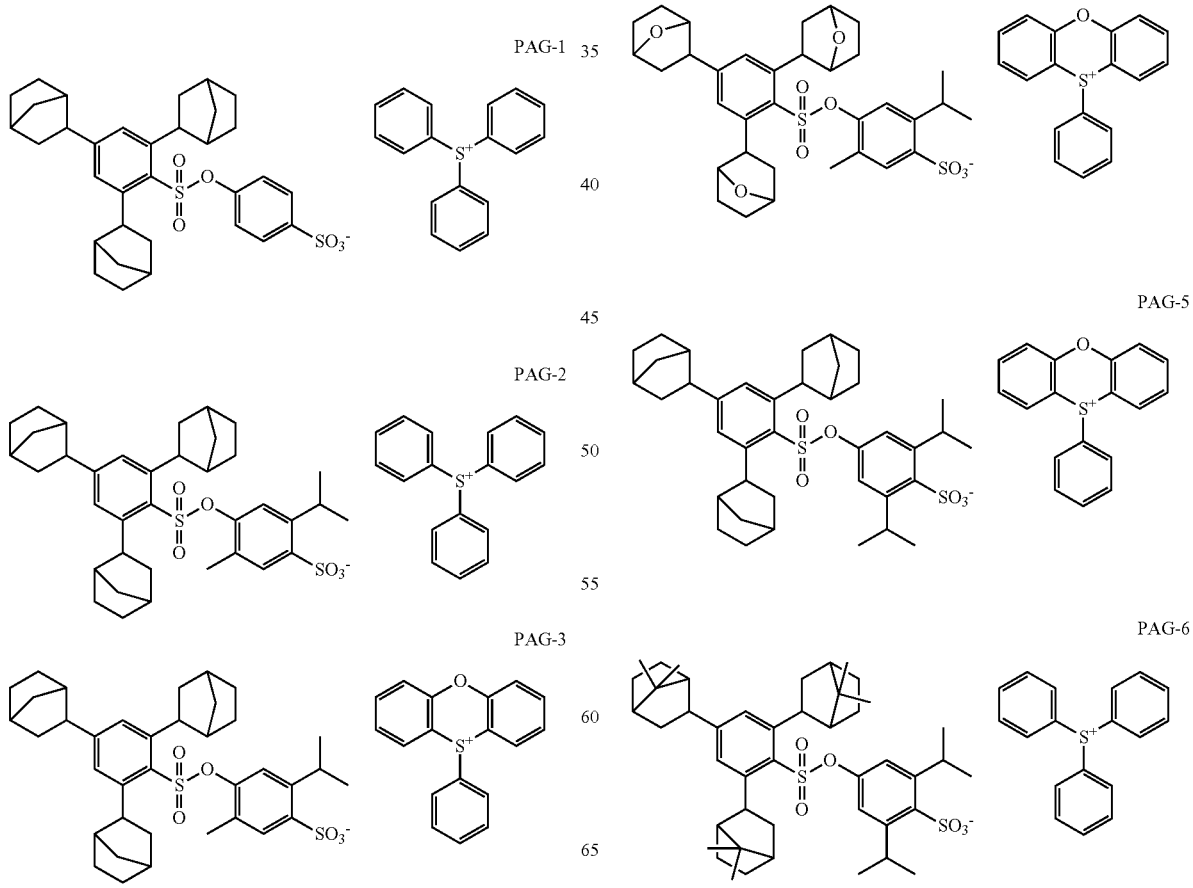

-continued
c-PAG-1
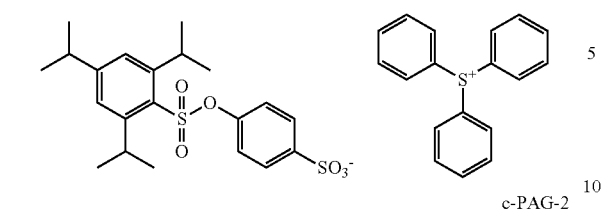
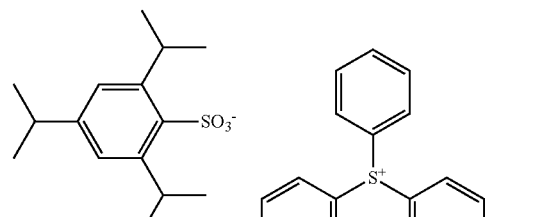
c-PAG-2
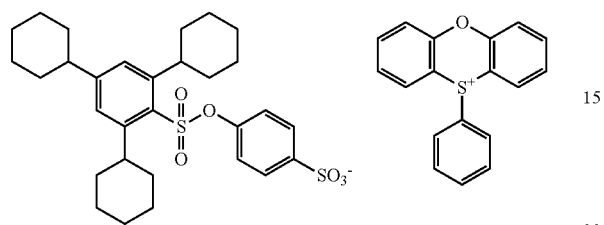
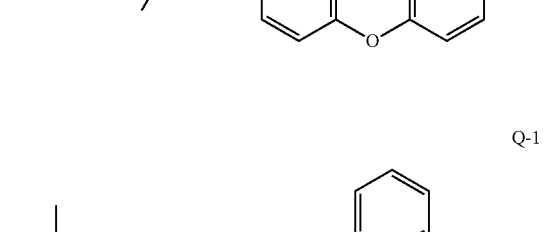
PAG-B
Q-1
c-PAG-3
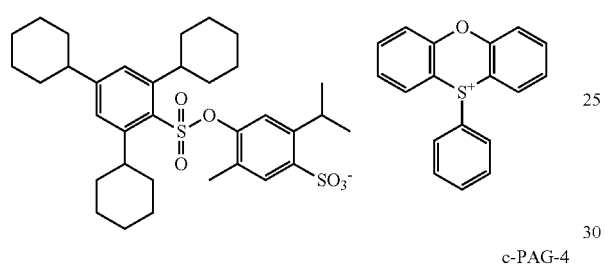
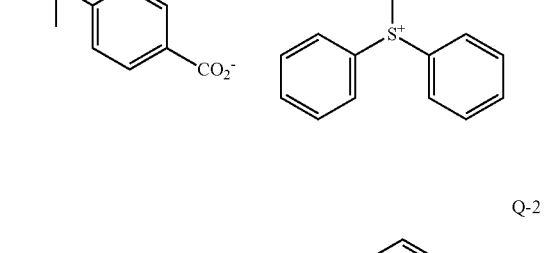
Q-2
c-PAG-4
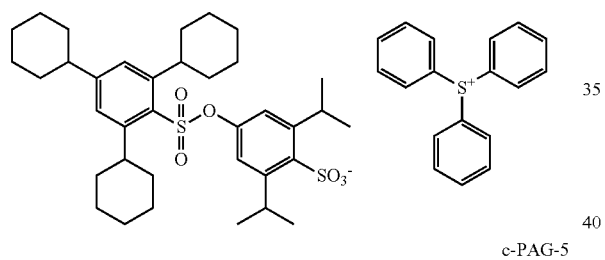
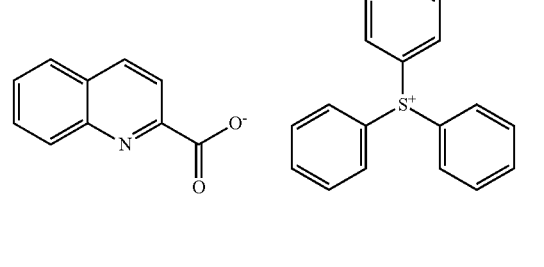
Q-3
c-PAG-5
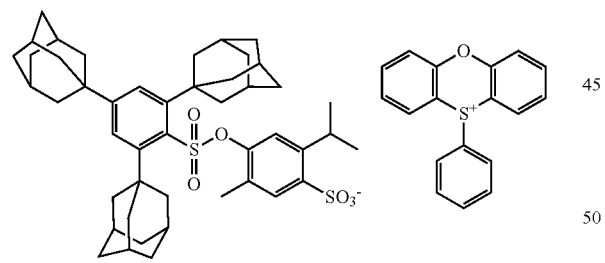
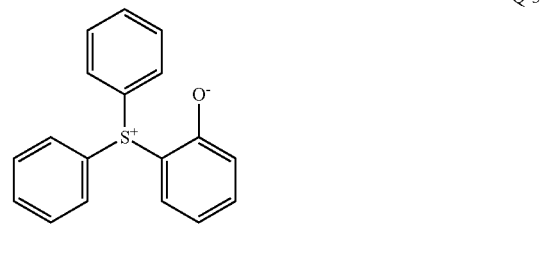
PAG-A
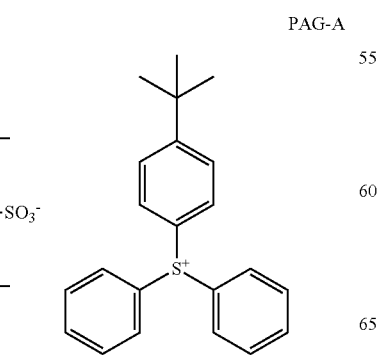
Polymer D1
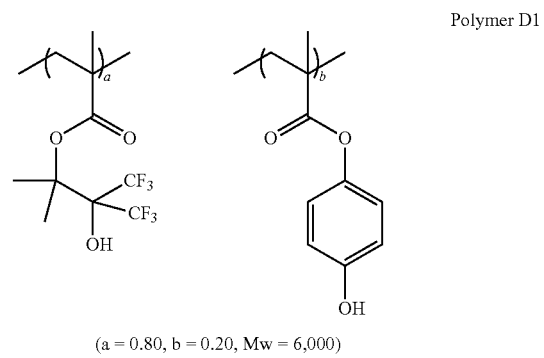
(a = 0.80, b = 0.20, Mw = 6,000)

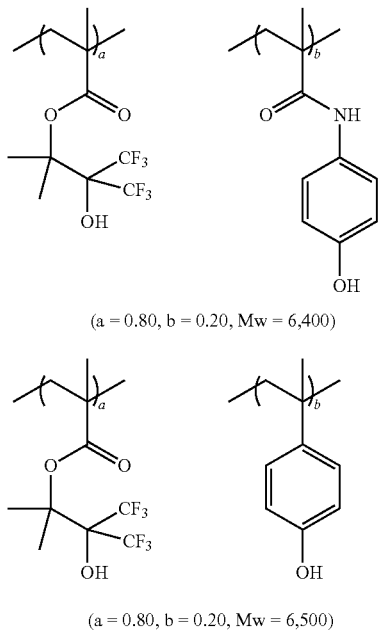

Polymer D2

(a = 0.80, b = 0.20, Mw = 6,400)

Polymer D3

(a = 0.80, b = 0.20, Mw = 6,500)

[4] EB Writing Test

Examples 3-1 to 3-34 and Comparative Examples 2-1 to 2-5

Using a coater/developer system ACT-M (Tokyo Electron Ltd.), each of the positive resist compositions (R-1 to R-34 and CR-1 to CR-5) was spin coated onto a mask blank of 152 mm squares having the outermost surface of chromium and prebaked on a hot plate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000Plus (NuFlare Technology Inc., accelerating voltage 50 kV), then baked (PEB) at 110° C. for 600 seconds, and developed in a 2.38 wt % tetramethylammonium hydroxide (TMAH) aqueous solution, thereby yielding positive patterns.

The patterned mask blank was observed under a top-down scanning electron microscope (TDSEM). The optimum exposure (Eop) was defined as the exposure dose ($\mu C/cm^2$) which provided a 1:1 resolution at the top and bottom of a 200-nm 1:1 line-and-space (LS) pattern. The maximum resolution of the resist was defined as the minimum line width of a LS pattern that could be resolved at the optimum exposure. The LER of a 200-nm LS pattern was measured under SEM. After a hole pattern with holes of 100 nm square was printed at the exposure dose which provides square resolution of 200 nm square pattern, a loss of area (area loss, %) at the corner of the hole pattern was measured under SEM. On observation in cross section of the resist pattern under SEM, it was visually judged whether or not the pattern profile was rectangular. The results are shown in Tables 9 and 10.

TABLE 9

| | | Resist composition | Eop, $\mu C/cm^2$ | Maximum resolution, nm | LER, nm | Area loss, % | Hole pattern profile |
|---|---|---|---|---|---|---|---|
| Example | 3-1 | R-1 | 50 | 35 | 4.8 | 13.0 | rectangular |
| | 3-2 | R-2 | 51 | 35 | 4.8 | 13.4 | rectangular |
| | 3-3 | R-3 | 52 | 35 | 4.7 | 12.5 | rectangular |
| | 3-4 | R-4 | 51 | 35 | 4.7 | 12.5 | rectangular |
| | 3-5 | R-5 | 48 | 35 | 4.6 | 13.1 | rectangular |
| | 3-6 | R-6 | 47 | 35 | 4.5 | 13.2 | rectangular |
| | 3-7 | R-7 | 50 | 35 | 4.6 | 12.8 | rectangular |
| | 3-8 | R-8 | 50 | 35 | 4.5 | 13.1 | rectangular |
| | 3-9 | R-9 | 47 | 40 | 4.7 | 13.3 | rectangular |
| | 3-10 | R-10 | 51 | 35 | 4.7 | 12.5 | rectangular |
| | 3-11 | R-11 | 50 | 35 | 4.6 | 12.7 | rectangular |
| | 3-12 | R-12 | 51 | 35 | 4.5 | 12.0 | rectangular |
| | 3-13 | R-13 | 51 | 40 | 4.9 | 13.5 | rectangular |
| | 3-14 | R-14 | 50 | 35 | 4.7 | 13.0 | rectangular |
| | 3-15 | R-15 | 52 | 40 | 4.8 | 13.1 | rectangular |
| | 3-16 | R-16 | 52 | 40 | 4.7 | 13.3 | rectangular |
| | 3-17 | R-17 | 50 | 35 | 4.7 | 13.1 | rectangular |
| | 3-18 | R-18 | 52 | 40 | 4.8 | 13.2 | rectangular |
| | 3-19 | R-19 | 51 | 35 | 4.7 | 13.1 | rectangular |
| | 3-20 | R-20 | 49 | 35 | 4.5 | 13.1 | rectangular |
| | 3-21 | R-21 | 50 | 35 | 4.5 | 13.0 | rectangular |
| | 3-22 | R-22 | 51 | 35 | 4.5 | 13.2 | rectangular |
| | 3-23 | R-23 | 51 | 35 | 4.6 | 13.2 | rectangular |
| | 3-24 | R-24 | 51 | 35 | 4.6 | 13.1 | rectangular |
| | 3-25 | R-25 | 53 | 40 | 4.8 | 12.9 | rectangular |
| | 3-26 | R-26 | 53 | 40 | 4.7 | 13.2 | rectangular |
| | 3-27 | R-27 | 52 | 40 | 4.8 | 12.9 | rectangular |
| | 3-28 | R-28 | 52 | 40 | 4.7 | 13.1 | rectangular |
| | 3-29 | R-29 | 51 | 35 | 4.7 | 12.8 | rectangular |
| | 3-30 | R-30 | 52 | 35 | 4.6 | 12.7 | rectangular |
| | 3-31 | R-31 | 50 | 35 | 4.5 | 12.6 | rectangular |
| | 3-32 | R-32 | 51 | 35 | 4.5 | 12.8 | rectangular |

TABLE 9-continued

|  | Resist composition | Eop, µC/cm$^2$ | Maximum resolution, nm | LER, nm | Area loss, % | Hole pattern profile |
|---|---|---|---|---|---|---|
| 3-33 | R-33 | 51 | 35 | 4.5 | 12.9 | rectangular |
| 3-34 | R-34 | 50 | 35 | 4.6 | 13.1 | rectangular |

TABLE 10

|  |  | Resist composition | Eop, µC/cm$^2$ | Maximum resolution, nm | LER, nm | Area loss, % | Hole pattern profile |
|---|---|---|---|---|---|---|---|
| Comparative Example | 2-1 | CR-1 | 48 | 45 | 5.2 | 22.1 | corner rounding |
|  | 2-2 | CR-2 | 48 | 45 | 5.0 | 19.3 | corner rounding |
|  | 2-3 | CR-3 | 49 | 40 | 4.9 | 18.8 | corner rounding |
|  | 2-4 | CR-4 | 50 | 40 | 4.8 | 18.4 | corner rounding |
|  | 2-5 | CR-5 | 52 | 50 | 5.3 | — | resist residues |

[5] EUV Exposure Test

Examples 4-1 to 4-3 and Comparative Example 3-1

Each of the positive resist compositions (R-35 to R-37 and CR-6) was spin coated on a silicon substrate (diameter 4 inches, vapor primed with hexamethyldisilazane (HMDS)) and prebaked on a hot plate at 105° C. for 60 seconds to form a resist film of 50 nm thick. EUV exposure was performed by dipole illumination at NA 0.3. Immediately after the exposure, the resist film was baked (PEB) on a hot plate for 60 seconds and puddle developed in a 2.38 wt % TMAH aqueous solution for 30 seconds to form a positive pattern.

The optimum exposure (Eop) is defined as the exposure dose that provides a 1:1 resolution of a 35-nm line-and-space pattern. Maximum resolution is a minimum size that can be resolved at Eop. The 35-nm LS pattern was measured for LER under SEM. On observation in cross section of the resist pattern under SEM, it was visually judged whether or not the pattern profile was rectangular. The results are shown in Table 11.

TABLE 11

|  |  | Resist composition | Eop, mJ/cm$^2$ | Maximum resolution, nm | LER, nm | Pattern profile |
|---|---|---|---|---|---|---|
| Example | 4-1 | R-35 | 14 | 26 | 4.1 | rectangular |
|  | 4-2 | R-36 | 14 | 28 | 4.0 | rectangular |
|  | 4-3 | R-37 | 15 | 26 | 4.1 | rectangular |
| Comparative Example | 3-1 | CR-6 | 14 | 30 | 4.5 | rectangular |

The results in Tables 9 to 11 are reviewed. The resist compositions of Examples 3-1 to 3-34, Examples 4-1 to 4-3, which contain onium salts of formula (1) within the scope of the invention, exhibit high resolution, satisfactory pattern rectangularity, and acceptable values of LER. In contrast, the resist compositions of Comparative Examples 2-1 to 2-4 form patterns with somewhat poor LER, and show corner rounding in hole pattern formation. Comparative Example 3-1 is inferior in LER to Examples. This is probably because the acid generated upon imagewise exposure diffuses to the unexposed region to incur the undesired reaction that some of the protective groups in the base polymer are deprotected. In Comparative Example 2-5 where the acid generator used is excessively lipophilic, resist residues are left after dissolution (development) in an attempt to form a hole pattern having holes which are as fine as 100 nm and uncompliant to resolution, and measurement is difficult.

The resist compositions containing onium salts of formula (1) are unsusceptible to the undesired reaction because the acid diffusion is reduced as compared with the resist compositions of Comparative Examples 2-1 to 2-4 containing comparative acid generators. Using the inventive resist composition, a hole pattern of satisfactory profile is formed.

It has been demonstrated that using the resist composition within the scope of the invention, a pattern of satisfactory rectangular profile having good maximum resolution, low LER, and a reduced area loss is formed. The pattern forming process using the resist composition within the scope of the invention is advantageous in the photolithography for semiconductor device fabrication and photomask blank processing.

Japanese Patent Application No. 2018-100517 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An onium salt having the formula (1):

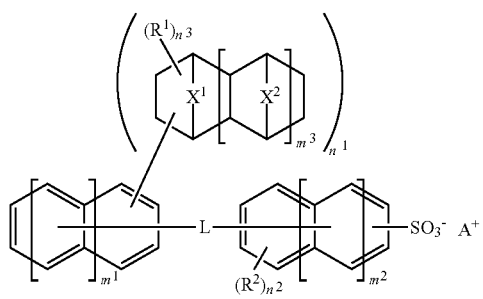

wherein $X^1$ and $X^2$ are each independently methylene, propane-2,2-diyl or ether bond, L is a single bond, ester bond, sulfonic acid ester bond, carbonate bond or carbamate bond, $R^1$ and $R^2$ are each independently a $C_1$-$C_{20}$ monovalent hydrocarbon group which may contain a heteroatom, $m^1$ and $m^2$ are each independently an integer of 0 to 2, $m^3$ is 0 or 1, $n^1$ is an integer satisfying $1 \leq n^1 \leq 5+2m^1$, $n^2$ is an integer satisfying $0 \leq n^2 \leq 4+2m^2$, $n^3$ is an integer satisfying $0 \leq n^3 \leq 8+4m^3$, $A^+$ is a sulfonium cation having the formula (2), an iodonium cation having the formula (3), or an ammonium cation having the formula (4):

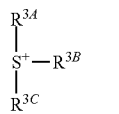

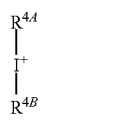

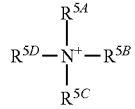

wherein $R^{3A}$, $R^{3B}$, $R^{3C}$, $R^{4A}$, $R^{4B}$, $R^{5A}$, $R^{5B}$ and $R^{5C}$ are each independently a $C_1$-$C_{20}$ monovalent hydrocarbon group which may contain a heteroatom, $R^{5D}$ is hydrogen or a $C_1$-$C_{20}$ monovalent hydrocarbon group which may contain a heteroatom, any two of $R^{3A}$, $R^{3B}$, and $R^{3C}$, or any two of $R^{5A}$, $R^{5B}$, $R^{5C}$, and $R^{5D}$ may bond together to form a ring with the sulfur or nitrogen atom to which they are attached.

2. A chemically amplified positive resist composition comprising (A) an acid generator containing the onium salt of claim 1 and (B) a base polymer containing a polymer adapted to be decomposed under the action of acid to increase its solubility in alkaline developer.

3. The resist composition of claim 2 wherein the polymer comprises recurring units having the formula (B1):

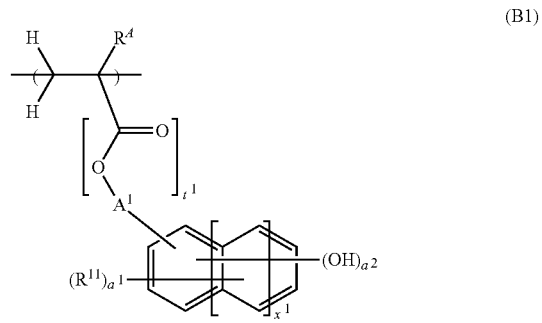

wherein $R^A$ is hydrogen, fluorine, methyl or trifluoromethyl, $R^{11}$ is each independently halogen, an optionally halogenated $C_2$-$C_8$ acyloxy group, optionally halogenated $C_1$-$C_6$ alkyl group, or optionally halogenated $C_1$-$C_6$ alkoxy group, $A^1$ is a single bond or $C_1$-$C_{10}$ alkanediyl group in which an ether bond may intervene in a carbon-carbon bond, $t^1$ is 0 or 1, $x^1$ is an integer of 0 to 2, $a^1$ is an integer satisfying $0 \leq a^1 \leq 5+2x^1-a^2$, and $a^2$ is an integer of 1 to 3.

4. The resist composition of claim 2 wherein the polymer comprises recurring units having the formula (B2):

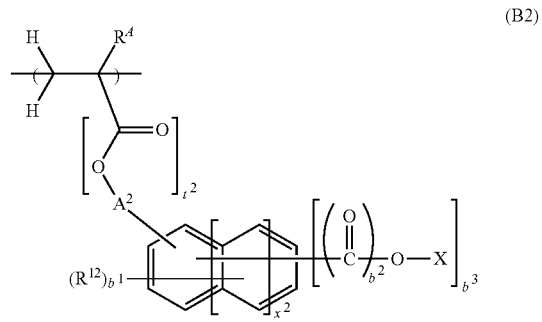

wherein $R^A$ is hydrogen, fluorine, methyl or trifluoromethyl, $R^{12}$ is each independently halogen, an optionally halogenated $C_2$-$C_8$ acyloxy group, optionally halogenated $C_1$-$C_6$ alkyl group, or optionally halogenated $C_1$-$C_6$ alkoxy group, $A^2$ is a single bond or $C_1$-$C_{10}$ alkanediyl group in which an ether bond may intervene in a carbon-carbon bond, $t^2$ is 0 or 1, $x^2$ is an integer of 0 to 2, $b^1$ is an integer satisfying $0 \leq b^1 \leq 5+2x^2-b^3$, $b^2$ is 0 or 1, $b^3$ is an integer of 1 to 3, X is an acid labile group in case of $b^3=1$, and X is each independently hydrogen or an acid labile group in case of $b^3=2$ or 3, at least one X being an acid labile group.

5. The resist composition of claim 2 wherein the polymer comprises recurring units of at least one type selected from units having the formulae (B3), (B4), and (B5):

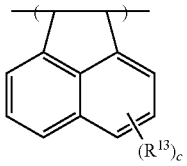 (B3)

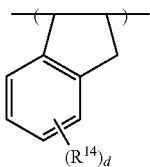 (B4)

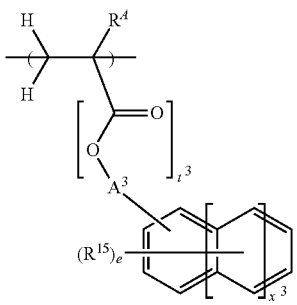 (B5)

wherein $R^A$ is hydrogen, fluorine, methyl or trifluoromethyl, $R^{13}$ and $R^{14}$ are each independently a hydroxyl group, halogen atom, acetoxy group, optionally halogenated $C_1$-$C_6$ alkyl group, optionally halogenated $C_1$-$C_6$ primary alkoxy group, optionally halogenated $C_2$-$C_6$ secondary alkoxy group, optionally halogenated $C_2$-$C_8$ acyloxy group, or optionally halogenated $C_2$-$C_8$ alkylcarbonyloxy group, $R^{15}$ is an acetyl group, acetoxy group, $C_1$-$C_{20}$ alkyl group, $C_1$-$C_{20}$ primary alkoxy group, $C_2$-$C_{20}$ secondary alkoxy group, $C_2$-$C_{20}$ acyloxy group, $C_2$-$C_{20}$ alkoxyalkyl group, $C_2$-$C_{20}$ alkylthioalkyl group, halogen atom, nitro group, or cyano group, $A^3$ is a single bond or $C_1$-$C_{10}$ alkanediyl group in which an ether bond may intervene in a carbon-carbon bond, c is an integer of 0 to 6, d is an integer of 0 to 4, e is an integer of 0 to 5, $t^3$ is 0 or 1, and $x^3$ is an integer of 0 to 2.

6. The resist composition of claim 2 wherein the polymer further comprises recurring units of at least one type selected from units having the formulae (B6) to (B11):

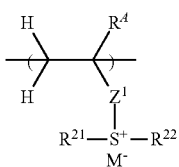 (B6)

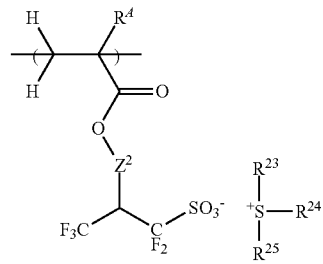 (B7)

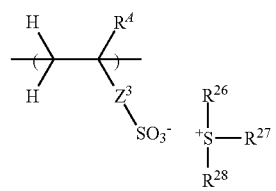 (B8)

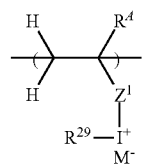 (B9)

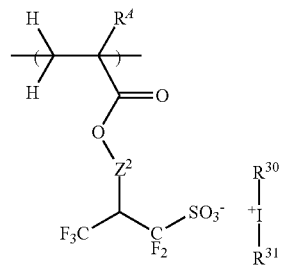 (B10)

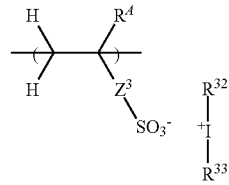 (B11)

wherein $R^A$ is hydrogen, fluorine, methyl or trifluoromethyl, $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl, $C_2$-$C_6$ alkenediyl or phenylene group, which may contain a carbonyl, ester bond, ether bond or hydroxyl moiety, $Z^2$ is a single bond or —$Z^{21}$—C(=O)—O—, $Z^{21}$ is a $C_1$-$C_{20}$ divalent hydrocarbon group which may contain a heteroatom, $Z^3$ is each independently a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ alkanediyl, $C_2$-$C_6$ alkenediyl or phenylene group, which may contain a carbonyl, ester bond, ether bond or hydroxyl moiety, $R^{21}$ to $R^{33}$ are each independently a $C_1$-$C_{20}$ monovalent hydrocarbon group which may contain a heteroatom, or $R^{21}$ and $R^{22}$ may bond together to form a ring with the sulfur atom to which they are attached, or any two of $R^{23}$, $R^{24}$ and $R^{25}$ may bond together to form a ring with the sulfur atom to which they are attached, any two of R²⁶, R²⁷ and R²⁸ may bond together to form a ring with the sulfur atom to which they are attached, and M⁻ is a non-nucleophilic counter ion.

7. The resist composition of claim 2, further comprising (C) an organic solvent.

8. The resist composition of claim 2, further comprising (D) a fluorinated polymer comprising recurring units having the formula (D) and recurring units of at least one type selected from units having the formulae (D2), (D3), (D4), and (D5):

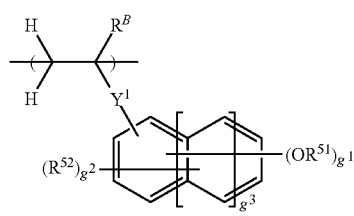
(D1)

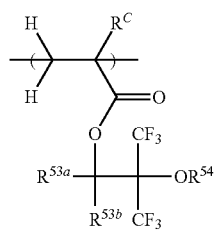
(D2)

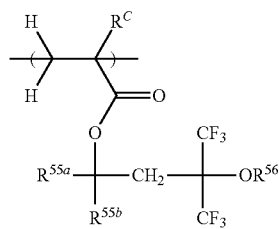
(D3)

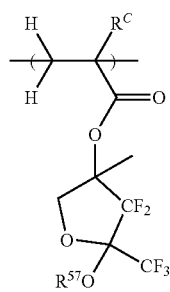
(D4)

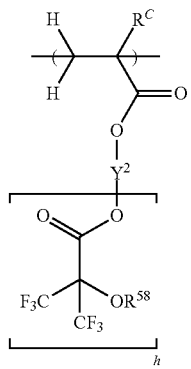
(D5)

wherein $R^B$ is hydrogen or methyl, $R^C$ is each independently hydrogen, fluorine, methyl or trifluoromethyl, $R^{51}$ is hydrogen or a $C_1$-$C_5$ straight or branched monovalent hydrocarbon group in which a heteroatom-containing moiety may intervene in a carbon-carbon bond, $R^{52}$ is a $C_1$-$C_5$ straight or branched monovalent hydrocarbon group in which a heteroatom-containing moiety may intervene in a carbon-carbon bond, $R^{53a}$, $R^{53b}$, $R^{55a}$ and $R^{55b}$ are each independently hydrogen or a $C_1$-$C_{10}$ alkyl group, $R^{54}$, $R^{56}$, $R^{57}$ and $R^{58}$ are each independently hydrogen, a $C_1$-$C_{15}$ monovalent hydrocarbon group, $C_1$-$C_{15}$ monovalent fluorinated hydrocarbon group, or an acid labile group, with the proviso that an ether bond or carbonyl moiety may intervene in a carbon-carbon bond in the monovalent hydrocarbon groups or monovalent fluorinated hydrocarbon groups represented by $R^{54}$, $R^{56}$, $R^{57}$ and $R^{58}$, $Y^1$ is a single bond, —C(=O)—O— or —C(=O)—NH—, $Y^2$ is a $C_1$-$C_{20}$ (h+1)-valent hydrocarbon group or $C_1$-$C_{20}$ (h+1)-valent fluorinated hydrocarbon group, $g^1$ is an integer of 1 to 3, $g^2$ is an integer satisfying $0 \leq g^2 \leq 5+2g^3-g^1$, $g^3$ is 0 or 1, and h is an integer of 1 to 3.

9. A resist pattern forming process comprising the steps of:
applying the resist composition of claim 2 onto a substrate to form a resist film thereon, exposing the resist film patternwise to high-energy radiation, and
developing the exposed resist film in an alkaline developer to form a resist pattern.

10. The process of claim 9 wherein the high-energy radiation is EUV or EB.

11. The process of claim 9 wherein the substrate has an outermost surface of chromium-containing material.

12. The process of claim 9 wherein the substrate is a photomask blank.

* * * * *